(12) United States Patent
Yang et al.

(10) Patent No.: US 7,700,772 B2
(45) Date of Patent: Apr. 20, 2010

(54) AMINO HETEROCYCLIC MODULATORS OF CHEMOKINE RECEPTOR ACTIVITY

(75) Inventors: Lihu Yang, Edison, NJ (US); Alexander Pasternak, Princeton, NJ (US); Sander G. Mills, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 830 days.

(21) Appl. No.: 10/589,406

(22) PCT Filed: Feb. 8, 2005

(86) PCT No.: PCT/US2005/003849

§ 371 (c)(1),
(2), (4) Date: Aug. 11, 2006

(87) PCT Pub. No.: WO2005/080371

PCT Pub. Date: Sep. 1, 2005

(65) Prior Publication Data

US 2007/0149529 A1 Jun. 28, 2007

Related U.S. Application Data

(60) Provisional application No. 60/544,763, filed on Feb. 12, 2004.

(51) Int. Cl.
C07D 401/04 (2006.01)
C07D 407/04 (2006.01)
A61K 31/445 (2006.01)
A61K 31/438 (2006.01)

(52) U.S. Cl. ............... 546/18; 546/207; 514/325; 514/278

(58) Field of Classification Search ............ 546/18, 546/207; 514/326, 278
See application file for complete search history.

(56) References Cited

U.S. PATENT DOCUMENTS 6,271,252 B1 8/2001 Chang et al.
6,432,947 B1 8/2002 Arnaiz et al.

*Primary Examiner*—Rita J Desai
(74) *Attorney, Agent, or Firm*—James L. McGinnis; Catherine D. Fitch

(57) ABSTRACT

Compounds of Formula I and Formula II: (wherein n, $R^1$, $R^2$, $R^3$, R4, $R^5$, $R^6$, $R^7$, $R^8$, $R^9$, $R^{10}$, $R^{15}$, $R^{16}$, $R^{17}$, $R^{18}$, $R^{19}$, $R^{24}$, $R^{25}$, $R^{26}$, $R^{27}$, $R^{28}$, $R^{29}$, $R^{30}$, $R^{33}$, $R^{34}$, $R^{35}$, $R^{36}$, $R^{37}$, $R^{38}$, A, j, k, m, n, X, Y and Z are as defined herein) which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

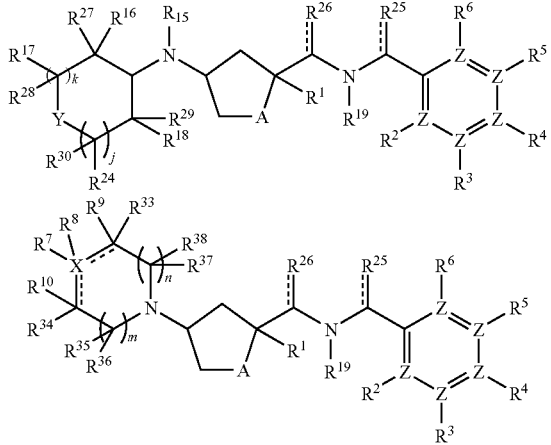

10 Claims, No Drawings

AMINO HETEROCYCLIC MODULATORS OF CHEMOKINE RECEPTOR ACTIVITY

RELATED APPLICATION DATA

This is a National filing under 35 USC 371 of PCT/US2005/003849, filed Feb. 8, 2005, which claims priority from U.S. Ser. No. 60/544,763, filed Feb. 12, 2004.

BACKGROUND OF THE INVENTION

The chemokines are a family of small (70-120 amino acids), proinflammatory cytokines, with potent chemotactic activities. Chemokines are chemotactic cytokines that are released by a wide variety of cells to attract various cells, such as monocytes, macrophages, T cells, eosinophils, basophils and neutrophils to sites of inflammation (reviewed in Schall, *Cytokine*, 3, 165-183 (1991) and Murphy, *Rev. Immun.*, 12, 593-633 (1994)). These molecules were originally defined by four conserved cysteines and divided into two subfamilies based on the arrangement of the first cysteine pair. In the CXC-chemokine family, which includes IL-8, GRO☐, NAP-2 and IP-10, these two cysteines are separated by a single amino acid, while in the CC-chemokine family, which includes RANTES, MCP-1, MCP-2, MCP-3, MIP-☐, MIP-1β and eotaxin, these two residues are adjacent.

The ☐-chemokines, such as interleukin-8 (IL-8), neutrophil-activating protein-2 (NAP-2) and melanoma growth stimulatory activity protein (MGSA) are chemotactic primarily for neutrophils, whereas ☐-chemokines, such as RANTES, MIP-☐, MIP-☐, monocyte chemotactic protein-1 (MCP-1), MCP-2, MCP-3 and eotaxin are chemotactic for macrophages, monocytes, T-cells, eosinophils and basophils (Deng, et al., *Nature*, 381, 661-666 (1996)).

The chemokines are secreted by a wide variety of cell types and bind to specific G-protein coupled receptors (GPCRs) (reviewed in Horuk, *Trends Pharm. Sci.*, 15, 159-165 (1994)) present on leukocytes and other cells. These chemokine receptors form a sub-family of GPCRs, which, at present, consists of fifteen characterized members and a number of orphans. Unlike receptors for promiscuous chemoattractants such as C5a, fMLP, PAF, and LTB4, chemokine receptors are more selectively expressed on subsets of leukocytes. Thus, generation of specific chemokines provides a mechanism for recruitment of particular leukocyte subsets.

On binding their cognate ligands, chemokine receptors transduce an intracellular signal though the associated trimeric G protein, resulting in a rapid increase in intracellular calcium concentration. There are at least seven human chemokine receptors that bind or respond to ☐-chemokines with the following characteristic pattern: CCR-1 (or "CKR-1" or "CC-CKR-1") [MIP-☐, MIP-☐, MCP-3, RANTES] (Ben-Barruch, et al., *J. Biol. Chem.*, 270, 22123-22128 (1995); Beote, et al, *Cell*, 72, 415-425 (1993)); CCR-2A and CCR-2B (or "CKR-2A"/"CKR-2A" or "CC-CKR-2A"/"CC-CKR-2A") [MCP-1, MCP-2, MCP-3, MCP-4]; CCR-3 (or "CKR-3" or "CC-CKR-3") [Eotaxin, Eotaxin 2, RANTES, MCP-2, MCP-3] (Rollins, et al., *Blood*, 90, 908-928 (1997)); CCR-4 (or "CKR-4" or "CC-CKR-4") [MIP-☐, RANTES, MCP-1] (Rollins, et al., *Blood*, 90, 908-928 (1997)); CCR-5 (or "CKR-5" or "CC-CKR-5") [MIP-☐, RANTES, MIP-☐] (Sanson, et al., *Biochemistry*, 35, 3362-3367 (1996)); and the Duffy blood-group antigen [RANTES, MCP-1] (Chaudhun, et al., *J. Biol. Chem.*, 269, 7835-7838 (1994)). The ☐chemokines include eotaxin, MIP ("macrophage inflammatory protein"), MCP ("monocyte chemoattractant protein") and RANTES ("regulation-upon-activation, normal T expressed and secreted") among other chemokines.

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. Humans who are homozygous for the 32-basepair deletion in the CCR-5 gene appear to have less susceptibility to rheumatoid arthritis (Gomez, et al., *Arthritis & Rheumatism*, 42, 989-992 (1999)). A review of the role of eosinophils in allergic inflammation is provided by Kita, H., et al., *J. Exp. Med.* 183, 2421-2426 (1996). A general review of the role of chemokines in allergic inflammation is provided by Lustger, A. D., *New England J. Med.*, 338(7), 426-445 (1998).

A subset of chemokines are potent chemoattractants for monocytes and macrophages. The best characterized of these is MCP-1 (monocyte chemoattractant protein-1), whose primary receptor is CCR2. MCP-1 is produced in a variety of cell types in response to inflammatory stimuli in various species, including rodents and humans, and stimulates chemotaxis in monocytes and a subset of lymphocytes. In particular, MCP-1 production correlates with monocyte and macrophage infiltration at inflammatory sites. Deletion of either MCP-1 or CCR2 by homologous recombination in mice results in marked attenuation of monocyte recruitment in response to thioglycollate injection and *Listeria monocytogenes* infection (Lu et al., *J. Exp. Med.*, 187, 601-608 (1998); Kurihara et al. *J. Exp. Med.*, 186, 1757-1762 (1997); Boring et al. *J. Clin. Invest.*, 100, 2552-2561 (1997); Kuziel et al. *Proc. Natl. Acad. Sci.*, 94, 12053-12058 (1997)). Furthermore, these animals show reduced monocyte infiltration into granulomatous lesions induced by the injection of schistosomal or mycobacterial antigens (Boring et al. *J. Clin. Invest.*, 100, 2552-2561 (1997); Warmington et al. *Am J. Path.*, 154, 1407-1416 (1999)). These data suggest that MCP-1-induced CCR2 activation plays a major role in monocyte recruitment to inflammatory sites, and that antagonism of this activity will produce a sufficient suppression of the immune response to produce therapeutic benefits in immunoinflammatory and autoimmune diseases.

Accordingly, agents which modulate chemokine receptors such as the CCR-2 receptor would be useful in such disorders and diseases.

In addition, the recruitment of monocytes to inflammatory lesions in the vascular wall is a major component of the pathogenesis of atherogenic plaque formation. MCP-1 is produced and secreted by endothelial cells and intimal smooth muscle cells after injury to the vascular wall in hypercholesterolemic conditions. Monocytes recruited to the site of injury infiltrate the vascular wall and differentiate to foam cells in response to the released MCP-1. Several groups have now demonstrated that aortic lesion size, macrophage content and necrosis are attenuated in MCP-1 –/– or CCR2 –/– mice backcrossed to APO-E –/–, LDL-R –/– or Apo B transgenic mice maintained on high fat diets (Boring et al. *Nature*, 394, 894-897 (1998); Gosling et al. *J. Clin. Invest.*, 103, 773-778 (1999)). Thus, CCR2 antagonists may inhibit atherosclerotic lesion formation and pathological progression by impairing monocyte recruitment and differentiation in the arterial wall.

SUMMARY OF THE INVENTION

The present invention is further directed to compounds of Formula I and Formula II:

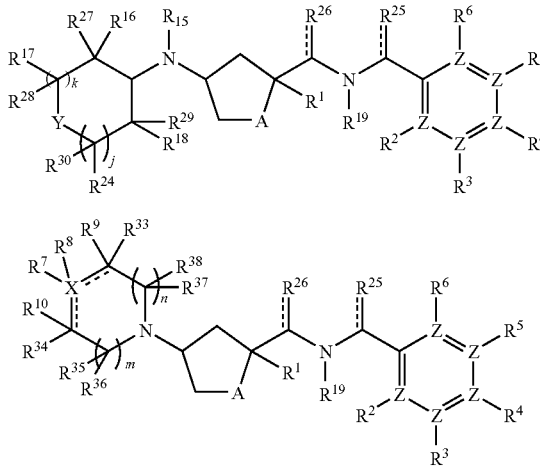

(wherein n, $R^1$, $R^2$, $R^3$, $R^4$, $R^5$, $R^6$, $R^7$, $R^8$, $R^9$, $R^{10}$, $R^{15}$, $R^{16}$, $R^{17}$, $R^{18}$, $R^{19}$, $R^{24}$, $R^{25}$, $R^{26}$, $R^{27}$, $R^{28}$, $R^{29}$, $R^{30}$, $R^{33}$, $R^{34}$, $R^{35}$, $R^{36}$, $R^{37}$, $R^{38}$, A, j, k, m, n, X, Y and Z are as defined herein) which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds of Formula I and Formula II:

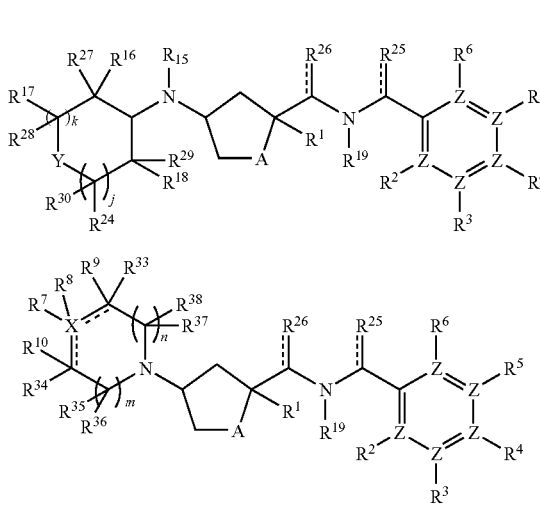

wherein:

A is selected from: —O—, —N($R^{20}$)—, —S—, —SO—, —$SO_2$—, —N($SO_2R^{14}$)—, and —N($COR^{13}$)—;

X is selected from O, N, S, $SO_2$ and C;
Y is selected from: —O—, —N($R^{20}$)—, —S—, —SO—, —$SO_2$—, —C($R^{21}$)($R^{22}$)—, —N($SO_2R^{14}$)—, —N($COR^{13}$)—, —C($R^{21}$)($COR^{11}$)—, —C($R^{21}$)($OCOR^{14}$)— and —CO—;
Z is C or N, where no more than three Z are N;
$R^1$ is selected from: hydrogen, —$C_{1-6}$alkyl, —O—$C_{1-6}$alkyl, —S—$C_{1-6}$alkyl, —SO—$C_{1-6}$alkyl, —$SO_2$—$C_{1-6}$alkyl, —$SO_2NR^{12}R^{12}$, —$NR^{12}$—$SO_2$—$NR^{12}R^{12}$, —($C_{0-6}$alkyl)-($C_{3-7}$cycloalkyl)-($C_{0-6}$alkyl), —CN, —$NR^{12}R^{12}$, —$NR^{12}COR^{13}$, —$NR^{12}SO_2R^{14}$, —$COR^{11}$, —$CONR^{12}R^{12}$, —$NR^{12}CONR^{12}R^{12}$, —O—CO—$C_{1-6}$alkyl, —O—$CO_2$—$C_{1-6}$alkyl, hydroxy, heterocycle and phenyl;
where said alkyl and cycloalkyl are unsubstituted or substituted with 1-7 substituents independently selected from: halo, hydroxy, —O—$C_{1-6}$alkyl unsubstituted or substituted with 1-6 fluoro, $C_{1-6}$alkyl unsubstituted or substituted with 1-6 fluoro, —$CONR^{12}R^{12}$, —$NR^{12}CONR^{12}R^{12}$, —$COR^{11}$, —$SO_2R^{14}$, —$NR^{12}COR^{13}$, —$NR^{12}SO_2R^{14}$, -heterocycle, =O, —CN, phenyl, —$SO_2NR^{12}R^{12}$, —$NR^{12}$—$SO_2$—$NR^{12}R^{12}$, —S—$C_{1-6}$alkyl unsubstituted or substituted with 1-6 fluoro, —SO—$C_{1-6}$alkyl unsubstituted or substituted with 1-6 fluoro, —$SO_2$—$C_{1-6}$alkyl unsubstituted or substituted with 1-6 fluoro and —O—$COR^{13}$,
where said phenyl and heterocycle are unsubstituted or substituted with 1-3 substituents independently selected from: halo, hydroxy, —$COR^{11}$, $C_{1-3}$alkyl substituted with 1-6 fluoro, $C_{1-3}$alkoxy unsubstituted or substituted with 1-6 fluoro, NHCOH and NHCO($C_{1-3}$alkyl);
$R^2$ is selected from: hydrogen, $C_{1-3}$alkyl unsubstituted or substituted with 1-3 fluoro, —O—$C_{1-3}$alkyl unsubstituted or substituted with 1-3 fluoro, hydroxy, chloro, fluoro, bromo, phenyl and heterocycle, when the Z bonded to $R^2$ is C, or $R^2$ is absent or is O when the Z bonded to $R^2$ is N;
$R^3$ is selected from: hydrogen, $C_{1-3}$alkyl unsubstituted or substituted with 1-3 fluoro, —O—$C_{1-3}$alkyl unsubstituted or substituted with 1-3 fluoro, hydroxy, chloro, fluoro, bromo, phenyl and heterocycle, when the Z bonded to $R^3$ is C, or $R^3$ is absent or is O when the Z bonded to $R^3$ is N;
$R^4$ is selected from: hydrogen, $C_{1-3}$alkyl unsubstituted or substituted with 1-3 fluoro, —O—$C_{1-3}$alkyl unsubstituted or substituted with 1-3 fluoro, hydroxy, chloro, fluoro, bromo, phenyl and heterocycle, when the Z bonded to $R^4$ is C, or $R^4$ is absent or is O when the Z bonded to $R^4$ is N;
$R^5$ is selected from: $C_{1-6}$alkyl unsubstituted or substituted with one or more substituents selected from 1-6 fluoro and hydroxyl, —O—$C_{1-6}$alkyl unsubstituted or substituted with 1-6 fluoro, —CO—$C_{1-6}$alkyl unsubstituted or substituted with 1-6 fluoro, —S—$C_{1-6}$alkyl unsubstituted or substituted with 1-6 fluoro, -pyridyl unsubstituted or substituted with one or more substituents selected from halo, trifluoromethyl, $C_{1-4}$alkyl and $COR^{11}$, fluoro, chloro, bromo, —$C_{4-6}$cycloalkyl, —O—$C_{4-6}$cycloalkyl, phenyl unsubstituted or substituted with one or more substituents selected from halo, trifluoromethyl, $C_{1-4}$alkyl and $COR^{11}$, —O-phenyl unsubstituted or substituted with one or more substituents selected from halo, trifluoromethyl, $C_{1-4}$alkyl and $COR^{11}$, —$C_{3-6}$cycloalkyl unsubstituted or substituted with 1-6 fluoro, —O—$C_{3-6}$cycloalkyl unsubstituted or substituted with 1-6 fluoro, -heterocycle, —CN and —$COR^{11}$, when the Z bonded to $R^5$ is C, or $R^5$ is absent or is O when the Z bonded to $R^5$ is N;
$R^6$ is selected from: hydrogen, $C_{1-3}$alkyl unsubstituted or substituted with 1-3 fluoro, —O—$C_{1-3}$alkyl unsubstituted or substituted with 1-3 fluoro, hydroxy, chloro, fluoro, bromo, phenyl and heterocycle, when the Z bonded to $R^6$ is C, or $R^6$ is absent or is O when the Z bonded to $R^6$ is N;

$R^7$ is selected from: hydrogen, $(C_{0-6}alkyl)$-phenyl, $(C_{0-6}$ alkyl)-heterocycle, $(C_{0-6}alkyl)$-$C_{3-7}$cycloalkyl, $(C_{0-6}$ alkyl)-$COR^{11}$, $(C_{0-6}alkyl)$-(alkene)-$COR^{11}$, $(C_{0-6}alkyl)$-$SO_3H$, $(C_{0-6}alkyl)$-W—$C_{0-4}$alkyl, $(C_{0-6}alkyl)$-$CONR^{12}$-phenyl and $(C_{0-6}alkyl)$-$CONR^{23}$—V—$COR^{11}$, when X is C or N, or $R^7$ is absent when X is O, S, or $SO_2$, where W is selected from: a single bond, —O—, —S—, —SO—, —$SO_2$—, —CO—, —$CO_2$—, —$CONR^{12}$— and —$NR^{12}$—, where V is selected from $C_{1-6}$alkyl and phenyl, where said $C_{0-6}$alkyl is unsubstituted or substituted with 1-5 substituents independently selected from: halo, hydroxy, —$C_{0-6}$alkyl, —O—$C_{1-3}$alkyl, trifluoromethyl and —$C_{0-2}$alkyl-phenyl, where said phenyl, heterocycle, cycloalkyl or $C_{0-4}$alkyl is unsubstituted or substituted with 1-5 substituents independently selected from: halo, trifluoromethyl, hydroxy, $C_{1-3}$alkyl, —O—$C_{1-3}$alkyl, —$C_{0-3}$—$COR^{11}$, —CN, —$NR^{12}R^{12}$, —$CONR^{12}R^{12}$ and —$C_{0-3}$-heterocycle, or said phenyl or said heterocycle is fused to a second heterocycle, said second heterocycle being unsubstituted or substituted with 1-2 substituents independently selected from hydroxy, halo, —$COR^{11}$, and —$C_{1-3}$alkyl, where said alkene is unsubstituted or substituted with 1-3 substituents independently selected from halo, trifluoromethyl, $C_{1-3}$alkyl, phenyl and heterocycle;

$R^8$ is selected from: hydrogen, hydroxy, $C_{1-6}$alkyl, $C_{1-6}$alkyl-hydroxy, —O—$C_{1-3}$alkyl, —$COR^{11}$, —$CONR^{12}R^{12}$ and —CN, when X is C, or $R^8$ is absent when X is O, S, $SO_2$ or N or when a double bond joins the carbons to which $R^7$ and $R^{10}$ are attached;

or, $R^7$ and $R^8$ join to form a ring selected from: 1H-indene, 2,3-dihydro-1H-indene, 2,3-dihydro-benzofuran, 1,3-dihydro-isobenzofuran, 2,3-dihydro-benzothiofuran, 1,3-dihydro-isobenzothiofuran, 6H-cyclopenta[d]isoxazol-3-ol, cyclopentane and cyclohexane, where said ring is unsubstituted or substituted with 1-5 substituents independently selected from: halo, trifluoromethyl, hydroxy, $C_{1-3}$alkyl, —O—$C_{1-3}$alkyl, —$C_{0-3}$—$COR^{11}$, —CN, —$NR^{12}R^{12}$, —$CONR^{12}R^{12}$ and —$C_{0-3}$-heterocycle;

$R^9$ and $R^{10}$ are independently selected from: hydrogen, hydroxy, $C_{1-6}$alkyl, $C_{1-6}$alkyl-$COR^{11}$, $C_{1-6}$alkyl-hydroxy, —O—$C_{1-3}$alkyl, =O (when $R^9$ or $R^{10}$ is connected to the ring via a double bond) and halo;

or, $R^7$ and $R^9$, or $R^8$ and $R^{10}$, join to form a ring which is phenyl or heterocycle, wherein said ring is unsubstituted or substituted with 1-7 substituents independently selected from: halo, trifluoromethyl, hydroxy, $C_{1-3}$alkyl, —O—$C_{1-3}$alkyl, —$COR^{11}$, —CN, —$NR^{12}R^{12}$ and —$CONR^{12}R^{12}$;

$R^{11}$ is independently selected from: hydroxy, hydrogen, $C_{1-6}$ alkyl, —O—$C_{1-6}$alkyl, benzyl, phenyl and $C_{3-6}$ cycloalkyl, where the alkyl, phenyl, benzyl, and cycloalkyl groups are unsubstituted or substituted with 1-6 substituents independently selected from: halo, hydroxy, $C_{1-3}$alkyl, $C_{1-3}$alkoxy, —$CO_2H$, —$CO_2$—$C_{1-6}$ alkyl, and trifluoromethyl;

$R^{12}$ is selected from: hydrogen, $C_{1-6}$ alkyl, benzyl, phenyl, and $C_{3-6}$ cycloalkyl, where said alkyl, phenyl, benzyl, and cycloalkyl groups are unsubstituted or substituted with 1-6 substituents independently selected from: halo, hydroxy, $C_{1-3}$alkyl, $C_{1-3}$alkoxy, —$CO_2H$, —$CO_2$—$C_{1-6}$ alkyl, and trifluoromethyl;

or, separate $R^{12}$ groups residing on the same or adjacent atoms together are $C_{1-7}$alkyl to form a ring, said $C_{1-7}$alkyl being unsubstituted or substituted with 1-6 substituents independently selected from: halo, hydroxy, $C_{1-3}$alkyl, $C_{1-3}$alkoxy, —$CO_2H$, —$CO_2$—$C_{1-6}$ alkyl, and trifluoromethyl;

$R^{13}$ is selected from: hydrogen, $C_{1-6}$ alkyl, —O—$C_{1-6}$alkyl, benzyl, phenyl and $C_{3-6}$ cycloalkyl, where said alkyl, phenyl, benzyl and cycloalkyl groups are unsubstituted or substituted with 1-6 substituents independently selected from: halo, hydroxy, $C_{1-3}$alkyl, $C_{1-3}$alkoxy, —$CO_2H$, —$CO_2$—$C_{1-6}$ alkyl and trifluoromethyl;

$R^{14}$ is selected from: hydroxy, $C_{1-6}$ alkyl, —O—$C_{1-6}$alkyl, benzyl, phenyl and $C_{3-6}$ cycloalkyl, where said alkyl, phenyl, benzyl, and cycloalkyl groups are unsubstituted or substituted with 1-6 substituents independently selected from: halo, hydroxy, $C_{1-3}$alkyl, $C_{1-3}$alkoxy, —$CO_2H$, —$CO_2$—$C_{1-6}$ alkyl, and trifluoromethyl;

$R^{15}$ is selected from: hydrogen and $C_{1-6}$alkyl, which is unsubstituted or substituted with 1-3 substituents independently selected from: halo, hydroxy, —$CO_2H$, —$CO_2C_{1-6}$alkyl, and —O—$C_{1-3}$alkyl;

$R^{16}$ is selected from: hydrogen, $C_{1-6}$alkyl unsubstituted or substituted with 1-6 substituents selected from: fluoro, $C_{1-3}$alkoxy, hydroxyl and —$COR^{11}$, fluoro, —O—$C_{1-3}$ alkyl unsubstituted or substituted with 1-3 fluoro, $C_{3-6}$ cycloalkyl, —O—$C_{3-6}$cycloalkyl, hydroxy, —$COR^1$ and —$OCOR^{13}$;

or, $R^{15}$ and $R^{16}$ join to form a 5-7 membered ring where $R^{15}$ and $R^{16}$ together are $C_{2-4}$alkyl or $C_{0-2}$alkyl-O—$C_{1-3}$alkyl;

$R^{17}$ is selected from: hydrogen, $C_{1-6}$alkyl unsubstituted or substituted with 1-6 substituents selected from fluoro, $C_{1-3}$alkoxy, hydroxyl and —$COR^{11}$, $COR^{11}$, hydroxy, and —O—$C_{1-6}$alkyl unsubstituted or substituted with 1-6 substituents selected from fluoro, $C_{1-3}$alkoxy, hydroxy, and —$COR^{11}$, or $R^{17}$ is absent when $R^{28}$ is O joined to a ring carbon via a double bond;

or, $R^{16}$ and $R^{17}$ join to form a 3-6 membered ring, where $R^{16}$ and $R^{17}$ together are $C_{1-4}$alkyl or $C_{0-3}$alkyl-O—$C_{0-3}$alkyl;

or, $R^{24}$ and $R^{17}$ join to form a 3-6 membered ring, where $R^{24}$ and $R^{17}$ together are $C_{1-4}$alkyl or $C_{0-3}$alkyl-O—$C_{0-3}$alkyl;

$R^{18}$ is selected from: hydrogen, $C_{1-6}$alkyl unsubstituted or substituted with 1-6 fluoro, fluoro, —O—$C_{3-6}$cycloalkyl and —O—$C_{1-3}$alkyl unsubstituted or substituted with 1-6 fluoro;

or, $R^{16}$ and $R^{18}$ join to form a 5-6 membered ring where $R^{16}$ and $R^{18}$ together are $C_{2-3}$alkyl, where said alkyl is unsubstituted or substituted with 1-3 substituents independently selected from halo, hydroxy, —$COR^{11}$, $C_{1-3}$alkyl, and $C_{1-3}$alkoxy;

or, $R^{16}$ and $R^{18}$ join to form a 6-8 membered ring, where $R^{16}$ and $R^{18}$ together are $C_{1-2}$alkyl-O—$C_{1-2}$alkyl, where said alkyl is unsubstituted or substituted with 1-3 substituents independently selected from halo, hydroxy, —$COR^{11}$, $C_{1-3}$alkyl and $C_{1-3}$alkoxy;

or, $R^{16}$ and $R^{18}$ join to form a 6-7 membered ring, where $R^{16}$ and $R^{18}$ together are —O—$C_{1-2}$alkyl-O—, where said alkyl is unsubstituted or substituted with 1-3 substituents independently selected from halo, hydroxy, —$COR^{11}$, $C_{1-3}$alkyl and $C_{1-3}$alkoxy;

$R^{19}$ is selected from: hydrogen, phenyl and $C_{1-6}$alkyl unsubstituted or substituted with 1-6 substituents selected from: —$COR^{11}$, hydroxy, fluoro, chloro and —O—$C_{1-3}$alkyl;

or, $R^2$ and $R^{19}$ join to form a heterocycle ring, where $R^2$ and $R^{19}$ together are selected from (with the left side of the linker being bonded to the amide nitrogen at $R^{19}$): —$CH_2$ $-(CR^{31}R^{31})_{1-3}-$, $-CH_2-NR^{32}-$, $-NR^{20}-CR^{31}R^{31}-$, $-CH_2O-$, $-CH_2SO_2-$, $-CH_2SO-$, $-CH_2S-$ and $-CR^{31}R^{31}-$;

$R^{20}$ is selected from: hydrogen, $C_{1-6}$ alkyl, benzyl, phenyl, $C_{3-6}$ cycloalkyl where the alkyl, phenyl, benzyl, and cycloalkyl groups can be unsubstituted or substituted with 1-6 substituents where the substituents are independently selected from: halo, hydroxy, $C_{1-3}$alkyl, $C_{1-3}$alkoxy, $-CO_2H$, $-CO_2-C_{1-6}$ alkyl, and trifluoromethyl;

$R^{21}$ and $R^{22}$ are independently selected from: hydrogen, hydroxy, $C_{1-6}$ alkyl, $-O-C_{1-6}$alkyl, benzyl, phenyl and $C_{3-6}$ cycloalkyl, where said alkyl, phenyl, benzyl and cycloalkyl groups are unsubstituted or substituted with 1-6 substituents independently selected from: halo, hydroxy, $C_{1-3}$alkyl, $C_{1-3}$alkoxy, $-CO_2H$, $-CO_2-C_{1-6}$ alkyl, and trifluoromethyl;

$R^{23}$ is hydrogen or $C_{1-4}$alkyl, or where $R^{23}$ is joined via $C_{1-5}$alkyl to one of the carbons of V to form a ring;

$R^{24}$ is selected from: hydrogen, $COR^{11}$, hydroxyl, $-O-C_{1-6}$ alkyl unsubstituted or substituted with 1-6 substituents selected from fluoro, $C_{1-3}$alkoxy, hydroxy, and $-COR^{11}$, and $C_{1-6}$alkyl unsubstituted or substituted with 1-6 substituents selected from fluoro, $C_{1-3}$alkoxy, hydroxyl and $-COR^{11}$;

$R^{25}$ and $R^{26}$ are independently selected from: $=O$ (where $R^{25}$ and/or $R^{26}$ is oxygen and is connected via a double bond), hydrogen, phenyl and $C_{1-6}$alkyl unsubstituted or substituted with 1-6 substituents selected from: $-COR^{11}$, hydroxy, fluoro, chloro and $-O-C_{1-3}$alkyl;

$R^{27}$, $R^{28}$, $R^{29}$, and $R^{30}$ are independently selected from: hydrogen, $COR^{11}$, hydroxy, $C_{1-6}$alkyl unsubstituted or substituted with 1-6 substituents selected from fluoro, $C_{1-3}$alkoxy, hydroxyl and $-COR^{11}$, and $-O-C_{1-6}$alkyl unsubstituted or substituted with 1-6 substituents selected from fluoro, $C_{1-3}$alkoxy, hydroxyl and $-COR^{11}$;

$R^{31}$ is independently selected from: hydrogen, $C_{1-3}$alkyl unsubstituted or substituted with 1-6 substituents independently selected from fluoro and hydroxy, $COR^{13}$, $SO_2R^{14}$, $SO_2NR^{12}R^{12}$, hydroxy, halo, $-NR^{12}R^{12}$, $-COR^{11}$, $-CONR^{12}R^{12}$, $-NR^{12}COR^{13}$, $-OCONR^{12}R^{12}$, $-NR^{12}CONR^{12}R^{12}$, -heterocycle, $-CN$, $-NR^{12}-SO_2-NR^{12}R^{12}$, $-NR^{12}-SO_2-R^{14}$, $-SO_2-NR^{12}R^{12}$, and $=O$ (where $R^{31}$ is connected to the ring via a double bond, in which case the other $R^{31}$ is nothing);

$R^{32}$ is selected from: hydrogen, $COR^{13}$, $SO_2R^{14}$, $SO_2NR^{12}R^{12}$ and $C_{1-3}$alkyl unsubstituted or substituted with 1-6 substituents independently selected from fluoro and hydroxyl;

$R^{33}$ and $R^{34}$ are independently selected from: hydrogen, hydroxy, $C_{1-6}$alkyl, $C_{1-6}$alkyl-$COR^{11}$, $C_{1-6}$alkyl-hydroxy, $-O-C_{1-3}$alkyl, trifluoromethyl and halo, or $R^{33}$ and $R^{34}$ are absent when the carbon to which they are bound unsaturated;

$R^{35}$ and $R^{38}$ are independently selected from: hydrogen, hydroxy, $C_{1-6}$alkyl, $C_{1-6}$alkyl-$COR^{11}$, $C_{1-6}$alkyl-hydroxy, $-O-C_{1-3}$alkyl, trifluoromethyl and halo;

$R^{36}$ and $R^{37}$ are independently selected from: hydroxy, $C_{1-6}$alkyl, $C_{1-6}$alkyl-$COR^{11}$, $C_{1-6}$alkyl-hydroxy, $-O-C_{1-3}$alkyl, halo and hydrogen, where said alkyl is unsubstituted or substituted with 1-6 substituents independently selected from fluoro and hydroxyl;

or, $R^{36}$ and $R^{37}$ join to form a ring, where $R^{36}$ and $R^{37}$ together are selected from $-C_{1-4}$alkyl-, $-C_{0-2}$alkyl-$O-C_{1-3}$alkyl- and $-C_{1-3}$alkyl-$O-CO-2$alkyl-; where said alkyls are unsubstituted or substituted with 1-2 substituents selected from of oxy (where the oxygen is joined to the ring via a double bond), fluoro, hydroxy, methoxy, methyl or trifluoromethyl;

j, k and m are independently 0, 1 or 2; n is 1 or 2;

a dashed line represents an optional single bond, whereby a dashed line used in conjunction with a solid line represents either a single or a double bond;

and pharmaceutically acceptable salts thereof and individual diastereomers thereof.

The present invention is also directed to compounds of Formula I and Formula II:

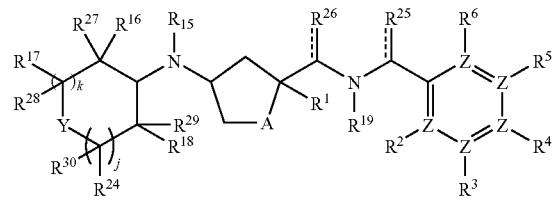

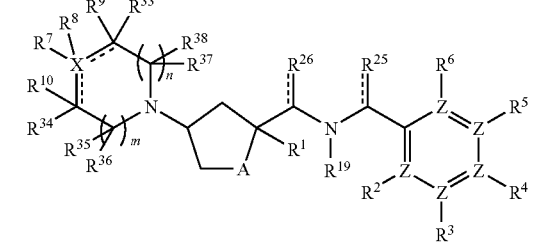

wherein:

A is selected from: $-O-$, $-N(R^{20})-$, $-S-$, $-SO-$, $-SO_2-$, $-N(SO_2R^{14})-$, and $-N(COR^{13})-$;

X is selected from O, N, S, $SO_2$ and C;

Y is selected from: $-O-$, $-N(R^{20})-$, $-S-$, $-SO-$, $-SO_2-$, $-C(R^{21})(R^{22})-$, $-N(SO_2R^{14})-$, $-N(COR^{13})-$, $-C(R^{21})(COR^{11})-$, $-C(R^{21})(OCOR^{14})-$ and $-CO-$;

Z is C or N, where no more than three Z are N.

$R^1$ is selected from: hydrogen, $-C_{1-6}$alkyl, $-O-C_{1-6}$alkyl, $-S-C_{1-6}$alkyl, $-SO-C_{1-6}$alkyl, $-SO_2-C_{1-6}$alkyl, $-SO_2NR^{12}R^{12}$, $-NR^{12}-SO_2-NR^{12}R^{12}$, $-(C_{0-6}$alkyl)-$(C_{3-7}$cycloalkyl)-$(C_{0-6}$alkyl), $-CN$, $-NR^{12}R^{12}$, $-NR^{12}COR^{13}$, $-NR^{12}SO_2R^{14}$, $-COR^{11}$, $-CONR^{12}R^{12}$, $-NR^{12}CONR^{12}R^{12}$, $-O-CO-C_{1-6}$alkyl, $-O-CO_2-C_{1-6}$alkyl, hydroxy, heterocycle and phenyl;

where said alkyl and cycloalkyl are unsubstituted or substituted with 1-7 substituents independently selected from: halo, hydroxy, $-O-C_{1-6}$alkyl unsubstituted or substituted with 1-6 fluoro, $C_{1-6}$alkyl unsubstituted or substituted with 1-6 fluoro, $-CONR^{12}R^{12}$, $-NR^{12}CONR^{12}R^{12}$, $-COR^{11}$, $-SO_2R^{14}$, $-NR^{12}COR^{13}$, $-NR^{12}SO_2R^{14}$, -heterocycle, $=O$, $-CN$, phenyl, $-SO_2NR^{12}R^{12}$, $-NR^{12}-SO_2-NR^{12}R^{12}$, $-S-C_{1-6}$alkyl unsubstituted or substituted with 1-6 fluoro, $-SO-C_{1-6}$alkyl unsubstituted or substituted with 1-6 fluoro, $-SO_2-C_{1-6}$alkyl unsubstituted or substituted with 1-6 fluoro and $-O-COR^{13}$, where said phenyl and heterocycle are unsubstituted or substituted with 1-3 substituents independently selected from: halo, hydroxy, $-COR^{11}$, $C_{1-3}$alkyl unsubstituted substituted with 1-6 fluoro, and $C_{1-3}$alkoxy unsubstituted or substituted with 1-6 fluoro;

$R^2$ is selected from: hydrogen, $C_{1-3}$alkyl unsubstituted or substituted with 1-3 fluoro, —O—$C_{1-3}$alkyl unsubstituted or substituted with 1-3 fluoro, hydroxy, chloro, fluoro, bromo, phenyl and heterocycle, when the Z bonded to $R^2$ is C, or $R^2$ is absent or is O when the Z bonded to $R^2$ is N;

$R^3$ is selected from: hydrogen, $C_{1-3}$alkyl unsubstituted or substituted with 1-3 fluoro, —O—$C_{1-3}$alkyl unsubstituted or substituted with 1-3 fluoro, hydroxy, chloro, fluoro, bromo, phenyl and heterocycle, when the Z bonded to $R^3$ is C, or $R^3$ is absent or is O when the Z bonded to $R^3$ is N;

$R^4$ is selected from: hydrogen, $C_{1-3}$alkyl unsubstituted or substituted with 1-3 fluoro, —O—$C_{1-3}$alkyl unsubstituted or substituted with 1-3 fluoro, hydroxy, chloro, fluoro, bromo, phenyl and heterocycle, when the Z bonded to $R^4$ is C, or $R^4$ is absent or is O when the Z bonded to $R^4$ is N;

$R^5$ is selected from: $C_{1-6}$alkyl unsubstituted or substituted with one or more substituents selected from 1-6 fluoro and hydroxyl, —O—$C_{1-6}$alkyl unsubstituted or substituted with 1-6 fluoro, —CO—$C_{1-6}$alkyl unsubstituted or substituted with 1-6 fluoro, —S—$C_{1-6}$alkyl unsubstituted or substituted with 1-6 fluoro, -pyridyl unsubstituted or substituted with one or more substituents selected from halo, trifluoromethyl, $C_{1-4}$alkyl and $COR^{11}$, fluoro, chloro, bromo, —$C_{4-6}$cycloalkyl, —O—$C_{4-6}$cycloalkyl, phenyl unsubstituted or substituted with one or more substituents selected from halo, trifluoromethyl, $C_{1-4}$alkyl and $COR^{11}$, —O-phenyl unsubstituted or substituted with one or more substituents selected from halo, trifluoromethyl, $C_{1-4}$alkyl and $COR^{11}$, —$C_{3-6}$cycloalkyl unsubstituted or substituted with 1-6 fluoro, —O—$C_{3-6}$cycloalkyl unsubstituted or substituted with 1-6 fluoro, -heterocycle, —CN and —$COR^{11}$, when the Z bonded to $R^5$ is C, or $R^5$ is absent or is O when the Z bonded to $R^5$ is N;

$R^6$ is selected from: hydrogen, $C_{1-3}$alkyl unsubstituted or substituted with 1-3 fluoro, —O—$C_{1-3}$alkyl unsubstituted or substituted with 1-3 fluoro, hydroxy, chloro, fluoro, bromo, phenyl and heterocycle, when the Z bonded to $R^6$ is C, or $R^6$ is absent or is O when the Z bonded to $R^6$ is N;

$R^7$ is selected from: hydrogen, ($C_{0-6}$alkyl)-phenyl, ($C_{0-6}$alkyl)-heterocycle, ($C_{0-6}$alkyl)-$C_{3-7}$cycloalkyl, ($C_{0-6}$alkyl)-$COR^{11}$, ($C_{0-6}$alkyl)-(alkene)-$COR^{11}$, ($C_{0-6}$alkyl)-$SO_3H$, ($C_{0-6}$alkyl)-W—$C_{0-4}$alkyl, ($C_{0-6}$alkyl)-$CONR^{12}$-phenyl and ($C_{0-6}$alkyl)-$CONR^{23}$—V—$COR^{11}$, when X is C or N, or $R^7$ is absent when X is O, S, or $SO_2$, where W is selected from: a single bond, —O—, —S—, —SO—, —$SO_2$—, —CO—, —$CO_2$—, —$CONR^{12}$— and —$NR^{12}$—, where V is selected from $C_{1-6}$alkyl and phenyl, where said $C_{0-6}$alkyl is unsubstituted or substituted with 1-5 substituents independently selected from: halo, hydroxy, —$C_{0-6}$alkyl, —O—$C_{1-3}$alkyl, trifluoromethyl and —$C_{0-2}$alkyl-phenyl, where said phenyl, heterocycle, cycloalkyl or $C_{0-4}$alkyl is unsubstituted or substituted with 1-5 substituents independently selected from: halo, trifluoromethyl, hydroxy, $C_{1-3}$alkyl, —O—$C_{1-3}$alkyl, —$C_{0-3}$—$COR^{11}$, —CN, —$NR^{12}R^{12}$, —$CONR^{12}R^{12}$ and —$C_{0-3}$-heterocycle, or said phenyl or said heterocycle is fused to a second heterocycle, said second heterocycle being unsubstituted or substituted with 1-2 substituents independently selected from hydroxy, halo, —$COR^{11}$, and —$C_{1-3}$alkyl, where said alkene is unsubstituted or substituted with 1-3 substituents independently selected from halo, trifluoromethyl, $C_{1-3}$alkyl, phenyl and heterocycle;

$R^8$ is selected from: hydrogen, hydroxy, $C_{1-6}$alkyl, $C_{1-6}$alkyl-hydroxy, —O—$C_{1-3}$alkyl, —$COR^{11}$, —$CONR^{12}R^{12}$ and —CN, when X is C, or $R^8$ is absent when X is O, S, $SO_2$ or N or when a double bond joins the carbons to which $R^7$ and $R^{10}$ are attached;

or, $R^7$ and $R^8$ join to form a ring selected from: 1H-indene, 2,3-dihydro-1H-indene, 2,3-dihydro-benzofuran, 1,3-dihydro-isobenzofuran, 2,3-dihydro-benzothiofuran, 1,3-dihydro-isobenzothiofuran, 6H-cyclopenta[d]isoxazol-3-ol, cyclopentane and cyclohexane, where said ring is unsubstituted or substituted with 1-5 substituents independently selected from: halo, trifluoromethyl, hydroxy, $C_{1-3}$alkyl, —O—$C_{1-3}$alkyl, —$C_{0-3}$—$COR^{11}$, —CN, —$NR^{12}R^{12}$, —$CONR^{12}R^{12}$ and —$C_{0-3}$-heterocycle;

$R^9$ and $R^{10}$ are independently selected from: hydrogen, hydroxy, $C_{1-6}$alkyl, $C_{1-6}$alkyl-$COR^{11}$, $C_{1-6}$alkyl-hydroxy, —O—$C_{1-3}$alkyl, =O (when $R^9$ or $R^{10}$ is connected to the ring via a double bond) and halo;

or, $R^7$ and $R^9$, or $R^8$ and $R^{10}$, join to form a ring which is phenyl or heterocycle, wherein said ring is unsubstituted or substituted with 1-7 substituents independently selected from: halo, trifluoromethyl, hydroxy, $C_{1-3}$alkyl, —O—$C_{1-3}$alkyl, —$COR^{11}$, —CN, —$NR^{12}R^{12}$ and —$CONR^{12}R^{12}$;

$R^{11}$ is independently selected from: hydroxy, hydrogen, $C_{1-6}$alkyl, —O—$C_{1-6}$alkyl, benzyl, phenyl and $C_{3-6}$cycloalkyl, where the alkyl, phenyl, benzyl, and cycloalkyl groups are unsubstituted or substituted with 1-6 substituents independently selected from: halo, hydroxy, $C_{1-3}$alkyl, $C_{1-3}$alkoxy, —$CO_2H$, —$CO_2$—$C_{1-6}$ alkyl, and trifluoromethyl;

$R^{12}$ is selected from: hydrogen, $C_{1-6}$ alkyl, benzyl, phenyl, and $C_{3-6}$ cycloalkyl, where said alkyl, phenyl, benzyl, and cycloalkyl groups are unsubstituted or substituted with 1-6 substituents independently selected from: halo, hydroxy, $C_{1-3}$alkyl, $C_{1-3}$alkoxy, —$CO_2H$, —$CO_2$—$C_{1-6}$ alkyl, and trifluoromethyl;

or, separate $R^{12}$ groups residing on the same or adjacent atoms together are $C_{1-7}$alkyl to form a ring, said $C_{1-7}$alkyl being unsubstituted or substituted with with 1-6 substituents independently selected from: halo, hydroxy, $C_{1-3}$alkyl, $C_{1-3}$alkoxy, —$CO_2H$, —$CO_2$-$C_{1-6}$ alkyl, and trifluoromethyl;

$R^{13}$ is selected from: hydrogen, $C_{1-6}$ alkyl, —O—$C_{1-6}$alkyl, benzyl, phenyl and $C_{3-6}$ cycloalkyl, where said alkyl, phenyl, benzyl and cycloalkyl groups are unsubstituted or substituted with 1-6 substituents independently selected from: halo, hydroxy, $C_{1-3}$alkyl, $C_{1-3}$alkoxy, —$CO_2H$, —$CO_2$—$C_{1-6}$ alkyl and trifluoromethyl;

$R^{14}$ is selected from: hydroxy, $C_{1-6}$ alkyl, —O—$C_{1-6}$alkyl, benzyl, phenyl and $C_{3-6}$ cycloalkyl, where said alkyl, phenyl, benzyl, and cycloalkyl groups are unsubstituted or substituted with 1-6 substituents independently selected from: halo, hydroxy, $C_{1-3}$alkyl, $C_{1-3}$alkoxy, —$CO_2H$, —$CO_2$—$C_{1-6}$ alkyl, and trifluoromethyl;

$R^{15}$ is selected from: hydrogen and $C_{1-6}$alkyl, which is unsubstituted or substituted with 1-3 substituents independently selected from: halo, hydroxy, —$CO_2H$, —$CO_2C_{1-6}$alkyl, and —O—$C_{1-3}$alkyl;

$R^{16}$ is selected from: hydrogen, $C_{1-6}$alkyl unsubstituted or substituted with 1-6 substituents selected from: fluoro, $C_{1-3}$alkoxy, hydroxyl and —$COR^{11}$, fluoro, —O—$C_{1-3}$ alkyl unsubstituted or substituted with 1-3 fluoro, $C_{3-6}$ cycloalkyl, —O—$C_{3-6}$cycloalkyl, hydroxy, —$COR^{11}$ and —$OCOR^{13}$;

or, $R^{15}$ and $R^{16}$ join to form a 5-7 membered ring where $R^{15}$ and $R^{16}$ together are $C_{2-4}$alkyl or $C_{0-2}$alkyl-O—$C_{1-3}$alkyl;

$R^{17}$ is selected from: hydrogen, $C_{1-6}$alkyl unsubstituted or substituted with 1-6 substituents selected from fluoro, $C_{1-3}$alkoxy, hydroxyl and —$COR^{11}$, $COR^{11}$, hydroxy, and —O—$C_{1-6}$alkyl unsubstituted or substituted with 1-6 substituents selected from fluoro, $C_{1-3}$alkoxy, hydroxy, and —$COR^{11}$, or $R^{17}$ is absent when $R^{28}$ is O joined to a ring carbon via a double bond;

or, $R^{16}$ and $R^{17}$ join to form a 3-6 membered ring, where $R^{16}$ and $R^{17}$ together are $C_{1-4}$alkyl or $C_{0-3}$alkyl-O—$C_{0-3}$alkyl;

or, $R^{24}$ and $R^{17}$ join to form a 3-6 membered ring, where $R^{24}$ and $R^{17}$ together are $C_{1-4}$alkyl or $C_{0-3}$alkyl-O—$C_{0-3}$alkyl;

$R^{18}$ is selected from: hydrogen, $C_{1-6}$alkyl unsubstituted or substituted with 1-6 fluoro, fluoro, —O—$C_{3-6}$cycloalkyl and —O—$C_{1-3}$alkyl unsubstituted or substituted with 1-6 fluoro;

or, $R^{16}$ and $R^{18}$ join to form a 5-6 membered ring where $R^{16}$ and $R^{18}$ together are $C_{2-3}$alkyl, where said alkyl is unsubstituted or substituted with 1-3 substituents independently selected from halo, hydroxy, —$COR^{11}$, $C_{1-3}$alkyl, and $C_{1-3}$alkoxy;

or, $R^{16}$ and $R^{18}$ join to form a 6-8 membered ring, where $R^{16}$ and $R^{18}$ together are $C_{1-2}$alkyl-O—$C_{1-2}$alkyl, where said alkyl is unsubstituted or substituted with 1-3 substituents independently selected from halo, hydroxy, —$COR^{11}$, $C_{1-3}$alkyl and $C_{1-3}$alkoxy;

or, $R^{16}$ and $R^{18}$ join to form a 6-7 membered ring, where $R^{16}$ and $R^{18}$ together are —O—$C_{1-2}$alkyl-O—, where said alkyl is unsubstituted or substituted with 1-3 substituents independently selected from halo, hydroxy, —$COR^{11}$, $C_{1-3}$alkyl and $C_{1-3}$alkoxy;

$R^{19}$ is selected from: hydrogen, phenyl and $C_{1-6}$alkyl unsubstituted or substituted with 1-6 substituents selected from: —$COR^{11}$, hydroxy, fluoro, chloro and —O—$C_{1-3}$alkyl;

or, $R^2$ and $R^{19}$ join to form a heterocycle ring, where $R^2$ and $R^{19}$ together are selected from (with the left side of the linker being bonded to the amide nitrogen at $R^{19}$): —$CH_2(CR^{31}R^{31})_{1-3}$—, —$CH_2$—$NR^{32}$—, —$NR^{20}$—$CR^{31}R^{31}$—, —$CH_2O$—, —$CH_2SO_2$—, —$CH_2SO$—, —$CH_2S$— and —$CR^{31}R^{31}$—;

$R^{20}$ is selected from: hydrogen, $C_{1-6}$ alkyl, benzyl, phenyl, $C_{3-6}$ cycloalkyl where the alkyl, phenyl, benzyl, and cycloalkyl groups can be unsubstituted or substituted with 1-6 substituents where the substituents are independently selected from: halo, hydroxy, $C_{1-3}$alkyl, $C_{1-3}$alkoxy, —$CO_2H$, —$CO_2$—$C_{1-6}$ alkyl, and trifluoromethyl;

$R^{21}$ and $R^{22}$ are independently selected from: hydrogen, hydroxy, $C_{1-6}$ alkyl, —O—$C_{1-6}$alkyl, benzyl, phenyl and $C_{3-6}$ cycloalkyl, where said alkyl, phenyl, benzyl and cycloalkyl groups are unsubstituted or substituted with 1-6 substituents independently selected from: halo, hydroxy, $C_{1-3}$alkyl, $C_{1-3}$alkoxy, —$CO_2H$, —$CO_2$—$C_{1-6}$ alkyl, and trifluoromethyl;

$R^{23}$ is hydrogen or $C_{1-4}$alkyl, or where $R^{23}$ is joined via $C_{1-5}$alkyl to one of the carbons of V to form a ring;

$R^{24}$ is selected from: hydrogen, $COR^{11}$, hydroxyl, —O—$C_{1-6}$ alkyl unsubstituted or substituted with 1-6 substituents selected from fluoro, $C_{1-3}$alkoxy, hydroxy, and —$COR^{11}$, and $C_{1-6}$alkyl unsubstituted or substituted with 1-6 substituents selected from fluoro, $C_{1-3}$alkoxy, hydroxyl and —$COR^{11}$;

$R^{25}$ and $R^{26}$ are independently selected from: =O (where $R^{25}$ and/or $R^{26}$ is oxygen and is connected via a double bond), hydrogen, phenyl and $C_{1-6}$alkyl unsubstituted or substituted with 1-6 substituents selected from: —$COR^{11}$, hydroxy, fluoro, chloro and —O—$C_{1-3}$alkyl;

$R^{27}$, $R^{28}$, $R^{29}$, and $R^{30}$ are independently selected from: hydrogen, $COR^{11}$, hydroxy, $C_{1-6}$alkyl unsubstituted or substituted with 1-6 substituents selected from fluoro, $C_{1-3}$alkoxy, hydroxyl and —$COR^{11}$, and —O—$C_{1-6}$alkyl unsubstituted or substituted with 1-6 substituents selected from fluoro, $C_{1-3}$alkoxy, hydroxyl and —$COR^{11}$;

$R^{31}$ is independently selected from: hydrogen, $C_{1-3}$alkyl unsubstituted or substituted with 1-6 substituents independently selected from fluoro and hydroxy, $COR^{13}$, $SO_2R^{14}$, $SO_2NR^{12}R^{12}$, hydroxy, halo, —$NR^{12}R^{12}$, —$COR^{11}$, —$CONR^{12}R^{12}$, —$NR^{12}COR^{13}$, —$OCONR^{12}R^{12}$, —$NR^{12}CONR^{12}R^{12}$, -heterocycle, —CN, —$NR^{12}$—$SO_2$-$NR^{12}R^{12}$, —$NR^{12}$—$SO_2$—$R^{14}$, —$SO_2$—$NR^{12}R^{12}$, and =O (where $R^{31}$ is connected to the ring via a double bond, in which case the other $R^{31}$ is nothing);

$R^{32}$ is selected from: hydrogen, $COR^{13}$, $SO_2R^{14}$, $SO_2NR^{12}R^{12}$ and $C_{1-3}$alkyl unsubstituted or substituted with 1-6 substituents independently selected from fluoro and hydroxyl;

$R^{33}$ and $R^{34}$ are independently selected from: hydrogen, hydroxy, $C_{1-6}$alkyl, $C_{1-6}$alkyl-$COR^{11}$, $C_{1-6}$alkyl-hydroxy, —O—$C_{1-3}$alkyl, trifluoromethyl and halo, or $R^{33}$ and $R^{34}$ are absent when the carbon to which they are bound unsaturated;

$R^{35}$ and $R^{38}$ are independently selected from: hydrogen, hydroxy, $C_{1-6}$alkyl, $C_{1-6}$alkyl-$COR^{11}$, $C_{1-6}$alkyl-hydroxy, —O—$C_{1-3}$alkyl, trifluoromethyl and halo;

$R^{36}$ and $R^{37}$ are independently selected from: hydroxy, $C_{1-6}$alkyl, $C_{1-6}$alkyl-$COR^{11}$, $C_{1-6}$alkyl-hydroxy, —O—$C_{1-3}$alkyl, halo and hydrogen, where said alkyl is unsubstituted or substituted with 1-6 substituents independently selected from fluoro and hydroxyl;

or, $R^{36}$ and $R^{37}$ join to form a ring, where $R^{36}$ and $R^{37}$ together are selected from —$C_{1-4}$alkyl-, —$C_{0-2}$alkyl-O—$C_{1-3}$alkyl- and —$C_{1-3}$alkyl-O—$C_{0-2}$alkyl-; where said alkyls are unsubstituted or substituted with 1-2 substituents selected from of oxy (where the oxygen is joined to the ring via a double bond), fluoro, hydroxy, methoxy, methyl or trifluoromethyl;

j, k and m are independently 0, 1 or 2;

n is 1 or 2;

a dashed line represents an optional single bond, whereby a dashed line used in conjunction with a solid line represents either a single or a double bond;

and pharmaceutically acceptable salts thereof and individual diastereomers thereof.

Compounds of the present invention also include compounds of Formula Ia:

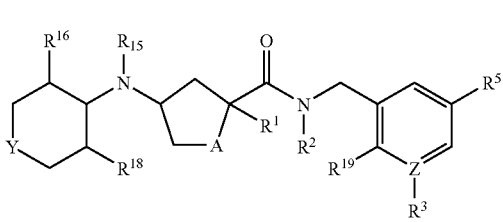

where $R^1$, $R^2$, $R^3$, $R^5$, $R^{15}$, $R^{16}$, $R^{18}$, $R^{19}$, A, Y, and Z are described herein.

More compounds of the present invention include compounds of Formula IIa:

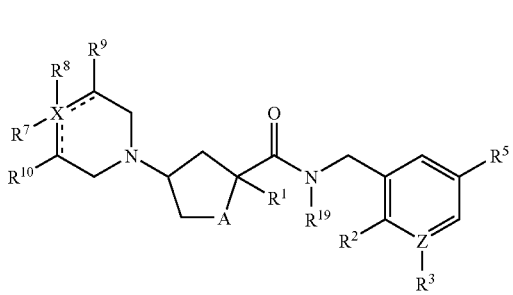

where $R^1$, $R^2$, $R^3$, $R^5$, $R^7$, $R^8$, $R^9$, $R^{10}$, $R^{19}$, A, X, and Z are described herein.

Still more compounds of the present invention include the compounds of Formula Ib:

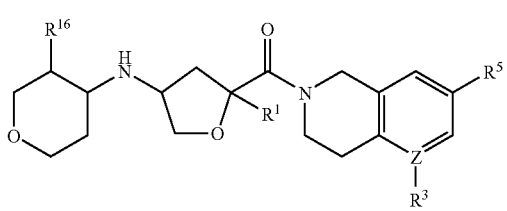

where $R^1$, $R^3$, $R^5$, $R^{16}$ and Z are described herein.

Certain embodiments of the present invention include those where A is N or O.

Other embodiments of the present invention include those where A is O.

Certain embodiments of the present invention include those where X is N, O or C.

Certain other embodiments of the present invention include those where X is C.

Certain embodiments of the present invention include those where Y is O or C.

Certain other embodiments of the present invention include those where Y is O.

Embodiments of the present invention include those where Z is N or C.

Embodiments of the present invention include those where $R^1$ is selected from: —$C_{1-6}$alkyl unsubstituted or substituted with 1-6 substituents independently selected from halo, hydroxy, —O—$C_{1-3}$alkyl and trifluoromethyl, —$C_{0-6}$alkyl-O—$C_{1-6}$alkyl- unsubstituted or substituted with 1-6 substituents independently selected from halo and trifluoromethyl, —$C_{0-6}$alkyl-S—$C_{1-6}$alkyl- unsubstituted or substituted with 1-6 substituents independently selected from halo and trifluoromethyl, —($C_{3-5}$cycloalkyl)-($C_{0-6}$alkyl) unsubstituted or substituted with 1-7 substituents independently selected from halo, hydroxy, —O—$C_{1-3}$alkyl and trifluoromethyl, phenyl unsubstituted or substituted with 1-3 substituents independently selected from halo, hydroxyl, $C_{1-3}$alkyl, $C_{1-3}$alkoxy and trifluoromethyl, and heterocycle unsubstituted or substituted with 1-3 substituents independently selected from halo, hydroxyl, $C_{1-3}$alkyl, $C_{1-3}$alkoxy, trifluoromethyl.

Embodiments of the present invention also include those where $R^1$ is selected from: —$C_{1-6}$alkyl unsubstituted or substituted with 1-6 substituents independently selected from halo, hydroxy, —O—$C_{1-3}$alkyl and trifluoromethyl, —$C_{0-6}$alkyl-O—$C_{1-6}$alkyl- unsubstituted or substituted with 1-6 substituents independently selected from halo and trifluoromethyl, —$C_{0-6}$alkyl-S—$C_{1-6}$alkyl- unsubstituted or substituted with 1-6 substituents independently selected from halo and trifluoromethyl, —($C_{3-5}$cycloalkyl)-($C_{0-6}$alkyl) unsubstituted or substituted with 1-7 substituents independently selected from halo, hydroxy, —O—$C_{1-3}$alkyl and trifluoromethyl, phenyl unsubstituted or substituted with 1-3 substituents independently selected from halo, hydroxyl, $C_{1-3}$alkyl, $C_{1-3}$alkoxy and trifluoromethyl, and heterocycle unsubstituted or substituted with 1-3 substituents independently selected from halo, hydroxyl, $C_{1-3}$alkyl, $C_{1-3}$alkoxy, trifluoromethyl, NHCOH and NHCO($C_{1-3}$alkyl);

Further embodiments of the present invention include those where $R^1$ is selected from: $C_{1-6}$alkyl, $C_{1-6}$alkyl-hydroxy, and $C_{1-6}$alkyl substituted with 1-6 fluoro.

Other embodiments of the present invention include those where $R^2$ is H or where $R^2$ and $R^{19}$ together are a $C_2$-alkyl chain.

Other embodiments of the present invention include those where, when Z is C, $R^3$ is selected from: hydrogen, trifluoromethyl, trifluoromethoxy, hydroxy, chloro, fluoro, bromo and phenyl.

Embodiments of the present invention include those where, when Z is N, $R^3$ is selected from O (forming an N-oxide) or is absent.

Embodiments of the present invention also include those where $R^4$ is H.

Other embodiments of the present invention include those where $R^5$ is selected from: hydrogen, trifluoromethyl, trifluoromethoxy, hydroxy, chloro, fluoro, bromo and phenyl.

Further embodiments of the present invention include those where $R^5$ is selected from: trifluoromethyl, trifluoromethoxy and phenyl.

In certain embodiments of the present invention $R^7$ is selected from phenyl, heterocycle, $C_{3-7}$cycloalkyl, $C_{1-6}$alkyl, —$COR^{11}$ and —CONH—V—$COR^{11}$, where V is $C_{1-6}$alkyl or phenyl, and where said phenyl, heterocycle, $C_{3-7}$cycloalkyl and $C_{1-6}$alkyl are unsubstituted or substituted with 1-5 substituents independently selected from: halo, trifluoromethyl, hydroxy, $C_{1-3}$alkyl, —O—$C_{1-3}$alkyl, —$COR^{11}$, —CN, -heterocycle and —$CONR^{12}R^{12}$.

In certain other embodiments of the present invention $R^7$ is selected from phenyl, heterocycle, $C_{1-4}$alkyl, —$COR^{11}$ and —CONH—V—$COR^{11}$, where V is $C_{1-6}$alkyl or phenyl, and where said phenyl, heterocycle, and $C_{1-4}$alkyl are unsubstituted or substituted with 1-3 substituents independently selected from: halo, hydroxy, $C_{1-3}$alkyl, —O—$C_{1-3}$alkyl, —$COR^{11}$ and -heterocycle.

In still other embodiments of the present invention $R^7$ is selected from: hydrogen, —$COR^{11}$, —$CONHCH_3$, phenyl and heterocycle.

In certain embodiments of the present invention, when X is C, $R^8$ is selected from: hydrogen, hydroxy, —CN, and fluoro.

In still other embodiments of the present invention $R^7$ and $R^8$ join to form a ring selected from 1H-indene and 2,3-dihydro-1H-indene, where said ring is unsubstituted or substituted with 1-3 substituents independently selected from: halo, hydroxy, $C_{1-3}$alkyl, —O—$C_{1-3}$alkyl, —$COR^{11}$ and -heterocycle.

In certain embodiments of the present invention $R^9$ and $R^{10}$ are independently selected from: hydrogen, hydroxy, —$CH_3$, —O—$CH_3$ and =O (where $R^9$ and/or $R^{10}$ are joined to the ring via a double bond).

In certain other embodiments of the present invention $R^9$ and $R^{10}$ are hydrogen.

In certain embodiments of the present invention $R^{15}$ is methyl or hydrogen.

In certain embodiments of the present invention $R^{16}$ is selected from: hydrogen, —O—$C_{1-3}$alkyl, fluoro, hydroxyl, and $C_{1-3}$alkyl unsubstituted or substituted with 1-6 fluoro.

In further embodiments of the present invention $R^{16}$ is selected from: hydrogen, trifluoromethyl, methyl, methoxy, ethoxy, ethyl, fluoro and hydroxy.

In certain embodiments of the present invention $R^{18}$ is selected from: hydrogen, methyl and methoxy.

In certain embodiments of the present $R^{16}$ and $R^{18}$ together are —$CH_2CH_2$— or —$CH_2CH_2CH_2$— (to form a cyclopentyl ring or a cyclohexyl ring).

In certain embodiments of the present invention $R^{26}$ is =O (where O is joined via a double bond.

In certain embodiments of the present invention, one or more of $R^6$, $R^8$, $R^{17}$, $R^{18}$, $R^{19}$, $R^{25}$, $R^{27}$, $R^{28}$, $R^{29}$, $R^{30}$, $R^{33}$, $R^{34}$, $R^{35}$, $R^{36}$ and $R^{38}$ is hydrogen.

In certain embodiments of the present invention m=0 or 1.

In certain embodiments of the present invention n=1 or 2.

The independent syntheses of diastereomers and enantiomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

The independent syntheses of diastereomers and enantiomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo.

As used herein, "alkyl" is intended to mean linear, branched and cyclic carbon structures having no double or triple bonds. $C_{1-8}$, as in $C_{1-8}$alkyl, is defined to identify the group as having 1, 2, 3, 4, 5, 6, 7 or 8 carbons in a linear or branched arrangement, such that $C_{1-8}$alkyl specifically includes methyl, ethyl, n-propyl, iso-propyl, n-butyl, iso-butyl, tert-butyl, pentyl, hexyl, heptyl and octyl. More broadly, $C_{a-b}$alkyl (where a and b represent whole numbers) is defined to identify the group as having a through b carbons in a linear or branched arrangement. $C_0$, as in $C_0$alkyl is defined to identify the presence of a direct covalent bond. "Cycloalkyl" is an alkyl, part or all of which forms a ring of three or more atoms.

The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyxidazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimnidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The term "ring" is employed herein to refer to the formation or existence of a cyclic structure of any type, including free standing rings, fused rings, and bridges formed on existing rings. Rings may be non-aromatic or aromatic. Moreover, the existence or formation of a ring structure is at times herein disclosed wherein multiple substituents are defined "together", as in "where $R^{16}$ and $R^{18}$ together are $C_{1-2}$alkyl-O—$C_{1-2}$alkyl". In this case a ring is necessarily formed regardless of whether the term "ring" is employed.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be prepared from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media such as ether, ethyl acetate, ethanol, isopropanol, or acetonitrile are employed. Suitable salts are found, e.g. in Remington's Pharmaceutical Sciences, 17th ed., Mack Publishing Company, Easton, Pa., 1985, p. 1418.

Specific compounds within the present invention include a compound which selected from the group consisting of those compounds described in the Examples, and pharmaceutically acceptable salts thereof and individual diastereomers thereof.

The subject compounds are useful in a method of modulating chemokine receptor activity in a patient in need of such modulation comprising the administration of an effective amount of the compound.

The present invention is directed to the use of the foregoing compounds as modulators of chemokine receptor activity. In particular, these compounds are useful as modulators of the chemokine receptors, in particular CCR-2.

The utility of the compounds in accordance with the present invention as modulators of chemokine receptor activity may be demonstrated by methodology known in the art, such as the assay for chemokine binding as disclosed by Van Riper, et al., *J. Exp. Med.*, 177, 851-856 (1993) which may be readily adapted for measurement of CCR-2 binding.

Receptor affinity in a CCR-2 binding assay was determined by measuring inhibition of $^{125}$I-MCP-1 to the endogenous CCR-2 receptor on various cell types including monocytes, THP-1 cells, or after heterologous expression of the cloned receptor in eukaryotic cells. The cells were suspended in binding buffer (50 mM HEPES, pH 7.2, 5 mM $MgCl_2$, 1 mM $CaCl_2$, and 0.50% BSA) with and added to test compound or DMSO and $^{125}$I-MCP-1 at room temperature for 1 h to allow binding. The cells were then collected on GFB filters, washed with 25 mM HEPES buffer containing 500 mM NaCl and cell bound $^{125}$I-MCP-1 was quantified.

In a chemotaxis assay chemotaxis was performed using T cell depleted PBMC isolated from venous whole or leukophoresed blood and purified by Ficoll-Hypaque centrifugation followed by rosetting with neuraminidase-treated sheep erythrocytes. Once isolated, the cells were washed with HBSS containing 0.1 mg/ml BSA and suspended at $1 \times 10^7$ cells/ml. Cells were fluorescently labeled in the dark with 2□M Calcien-AM (Molecular Probes), for 30 min at 37° C. Labeled cells were washed twice and suspended at $5 \times 10^6$ cells/ml in RPMI 1640 with L-glutamine (without phenol red) containing 0.1 mg/ml BSA. MCP-1 (Peprotech) at 10 ng/ml diluted in same medium or medium alone were added to the bottom wells (27□). Monocytes (150,000 cells) were added to the topside of the filter (30□) following a 15 min preincubation with DMSO or with various concentrations of test compound. An equal concentration of test compound or DMSO was added to the bottom well to prevent dilution by diffusion. Following a 60 min incubation at 37° C., 5% $CO_2$, the filter was removed and the topside was washed with HBSS containing 0.1 mg/ml BSA to remove cells that had not migrated into the filter. Spontaneous migration (chemokinesis) was determined in the absence of chemoattractant In particular, the compounds of the following examples had activity in binding to the CCR-2 receptor in the aforementioned assays, generally with an $IC_{50}$ of less than about 1□M Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, compounds which inhibit or promote chemokine receptor function would be useful in treating, preventing, ameliorating, controlling or reducing the risk of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the compounds of the present invention. In a certain embodiment, the disease or condition is one in which the actions of lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogrer's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with modulators of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms), (Trichuriasis, Enterobiasis, Ascariasis, Hookworm, Strongyloidiasis, Trichinosis, filariasis), trematodes (flukes) (Schistosomiasis, Clonorchiasis), cestodes (tape worms) (Echinococcosis, Taeniasis saginata, Cysticercosis), visceral worms, visceral larva migraines (e.g., *Toxocara*), eosinophilic gastroenteritis (e.g., *Anisaki* sp., *Phocanema* sp.), and cutaneous larva migraines (*Ancylostona braziliense, Ancylostoma caninum*). In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

The compounds of the present invention are accordingly useful in treating, preventing, ameliorating, controlling or reducing the risk of a wide variety of inflammatory and immunoregulatory disorders and diseases, allergic conditions, atopic conditions, as well as autoimmune pathologies. In a specific embodiment, the present invention is directed to the use of the subject compounds for treating, preventing, ameliorating, controlling or reducing the risk of autoimmune diseases, such as rheumatoid arthritis or psoriatic arthritis.

In another aspect, the instant invention may be used to evaluate putative specific agonists or antagonists of chemokine receptors, including CCR-2. Accordingly, the present invention is directed to the use of these compounds in the preparation and execution of screening assays for compounds that modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-2. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of the present compounds in treating, preventing, ameliorating, controlling or reducing the risk of infection by a retrovirus, in particular, herpes virus or the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a further aspect of the present invention, a subject compound may be used in a method of inhibiting the binding of a chemokine to a chemokine receptor, such as CCR-2, of a target cell, which comprises contacting the target cell with an amount of the compound which is effective at inhibiting the binding of the chemokine to the chemokine receptor.

The subject treated in the methods above is a mammal, for instance a human being, male or female, in whom modulation of chemokine receptor activity is desired. "Modulation" as used herein is intended to encompass antagonism, agonism, partial antagonism, inverse agonism and/or partial agonism. In an aspect of the present invention, modulation refers to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration" of and or "administering a" compound should be understood to mean providing a compound of the invention to the individual in need of treatment.

As used herein, the term "treatment" refers both to the treatment and to the prevention or prophylactic therapy of the aforementioned conditions.

Combined therapy to modulate chemokine receptor activity for thereby treating, preventing, ameliorating, controlling or reducing the risk of inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in treating, preventing, ameliorating, controlling or reducing the risk of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codeine, embrel, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention may be used. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, desloratadine, cetirizine, fexofenadine, descarboethoxyloratadine, and the like; (e) non-steroidal anti-asthmatics such as □-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CCR-1, CCR-2, CCR-3, CXCR-3 and CCR-5; (j) cholesterol lowering agents such as HMG-CoA reductase inhibitors (lovastatin, simvastatin and pravastatin, fluvastatin, atorvastatin, rosuvastatin, and other statins), sequestrants (cholestyramine and colestipol), cholesterol absorption inhibitors (ezetimibe), nicotinic acid, fenofibric acid derivatives (gemfibrozil, clofibrat, fenofibrate and benzafibrate), and probucol; (k) antidiabetic agents such as insulin, sulfonylureas, biguanides (metformin), □-glucosidase inhibitors (acarbose) and glitazones (troglitazone and pioglitazone); (l) preparations of interferon beta (interferon beta-□, interferon beta-□); (m) other compounds such as 5-aminosalicylic acid and prodrugs thereof, antimetabolites such as azathioprine and 6-mercaptopurine, and cytotoxic cancer chemotherapeutic agents.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracistemal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In treating, preventing, ameliorating, controlling or reducing the risk of conditions which require chemokine receptor modulation an appropriate dosage level will generally be about 0.01 to 500 mg per kg patient body weight per day which can be administered in single or multiple doses. In certain embodiments the dosage level will be about 0.1 to about 250 mg/kg per day; or from about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, or 2.0 to 500, or 3.0 to 200, particularly 1, 5, 10, 15, 20, 25, 30, 50, 75, 100, 125, 150, 175, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, or once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are either commercially available or made by known procedures in the literature or as illustrated. The present invention further provides processes for the preparation of compounds of the formula I or of the formula II as defined above, which comprises many different sequences of assembling compounds of formula (IV), formula (V), and formula (III); or formula (VI), formula (V), and formula (III).

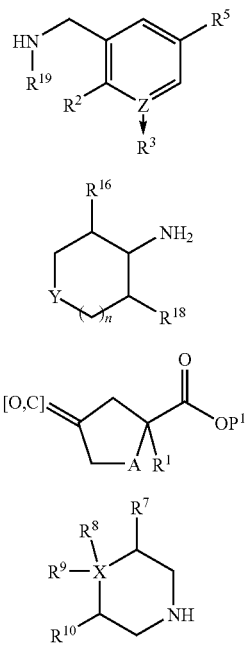

wherein $R^1$, $R^2$, $R^3$, $R^5$, $R^7$, R8, R9, $R^{10}$, $R^{16}$, $R^{18}$, $R^{19}$, A, Y, Z, and X are defined as in formula I, and $P^1$ represents either a hydrogen or an alkyl group such as methyl, ethyl, t-butyl, or benzyl which serves as a protecting group, (Greene, T; Wuts, P. G. M. *Protective Groups in Organic Synthesis*, John Wiley & Sons, Inc., New York, N.Y. 1991).

One general way of constructing target compounds I and II utilizing Intermediates of the formulas V, III, and IV for compounds I, and utilizing Intermediates of the formula V, VI, and II for compounds II are illustrated in Scheme 1. Coupling of the acid Va and the amine III under standard amide bond formation reaction conditions such as PyBrop in the presence of a base such as N,N-diisopropylethylamine and a catalyst such as DMAP gives the intermediate 1-1. Ozonolysis of the exo-olefin yields the keto-amide 1-2. Reductive amination of 1-2 with amines IV in the presence of a borohydride such as sodium triacetoxyborohydride or sodium cyanoborohydride then provides the compound of formula I. Note that when $R^{16}$ or $R^{18}$ are other than hydrogen, a mixture of diastereomers (Eliel, E. E., Wilen, S. H., *Stereochemristry of Organic Conmpounds*, John Wiley & Sons, Inc., New York) results from the reductive amination step. These can be separated into their components by chromatography using normal phase, reverse phase or chiral columns, depending on the nature of the separation. Compound I can be further elaborated to the compounds of the formula I by reductive alkylation with an aldehyde or by alkylation with, for example, an alkyl halide. Reductive amination of 1-2 with amines VI in the presence of a borohydride such as sodium triacetoxyborohydride or sodium cyanoborohydride would provide the compound of formula II.

SCHEME 1

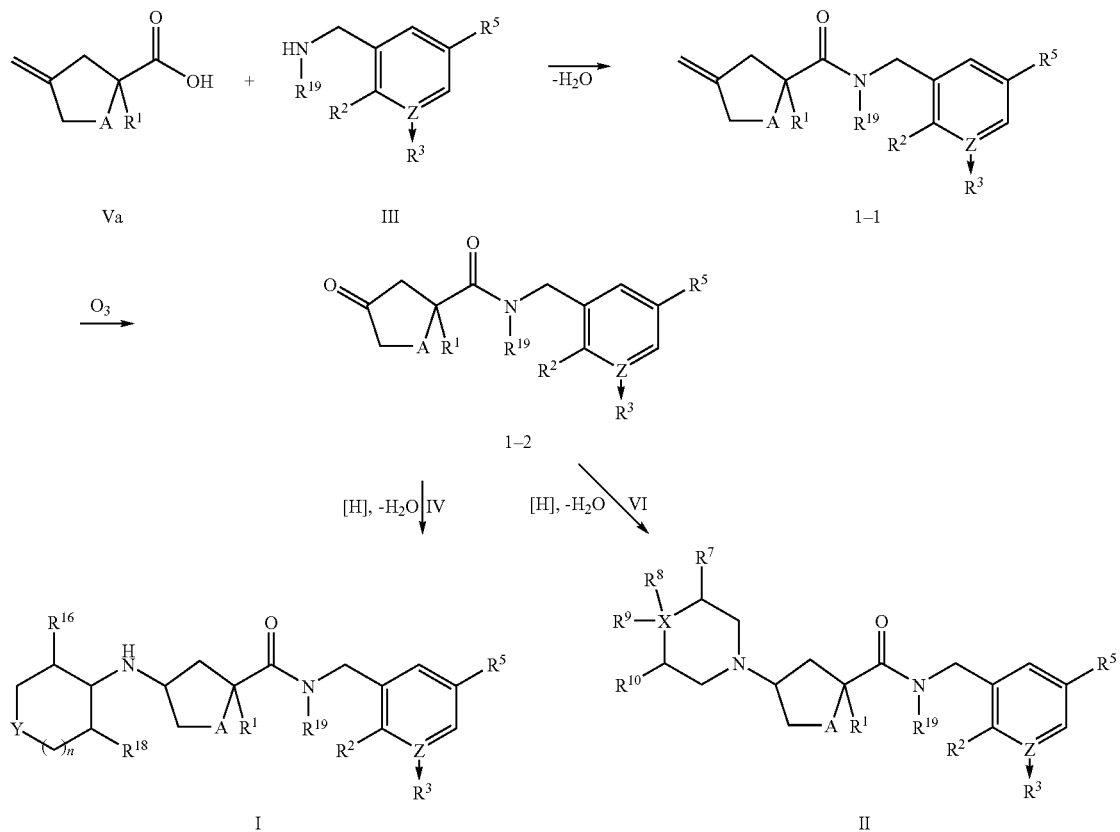

An alternate way of constructing compound I and is illustrated in Scheme 2. Coupling of the acid Vb and the amine III under standard amide bond formation reaction conditions such as PyBrop in the presence of a base such as N,N-diisopropylethylamine and a catalyst such as DMAP gives the intermediate 1-2. Reductive amination of 1-2 with amines IV in the presence of a borohydride such as sodium triacetoxyborohydride or sodium cyanoborohydride then provides the compound of formula Ia. Compound I can be further elaborated to the compounds of the formula I by reductive alkylation with an aldehyde or by alkylation with, for example, an alkyl halide. Reductive amination of 2-1 with amines VI in the presence of a borohydride such as sodium triacetoxyborohydride or sodium cyanoborohydride then provides the compound of formula Ia.

ero esters 3-1 (where $A^1$ is either OH or NHBoc) can be doubly alkylated with 3-chloro-2-chloromethyl-1-propene in the presence of a base such as sodium hydride in a solvent such as DMF to give cyclic esters 3-2. Deprotection of the ester by basic hydrolysis (if $P^1$ is ethyl or methyl) or under acidic conditions (if $P^1$ is t-butyl) gives acids Va. Alternativiely olefin 3-2 can be ozonized and reduced, with reducing agents such as dimethyl sulfide or triphenyl phosphine, to the keto ester 3-3. Esters 3-3 can then be deprotected to form acids Vb. Deprotection of the ester can be achieved by a number of methods depending upon the protecting group. If $P^1$ is methyl or ethyl, deprotection can be achieved by basic hydrolysis. If $P^1$ is t-butyl, deprotection can be achieved

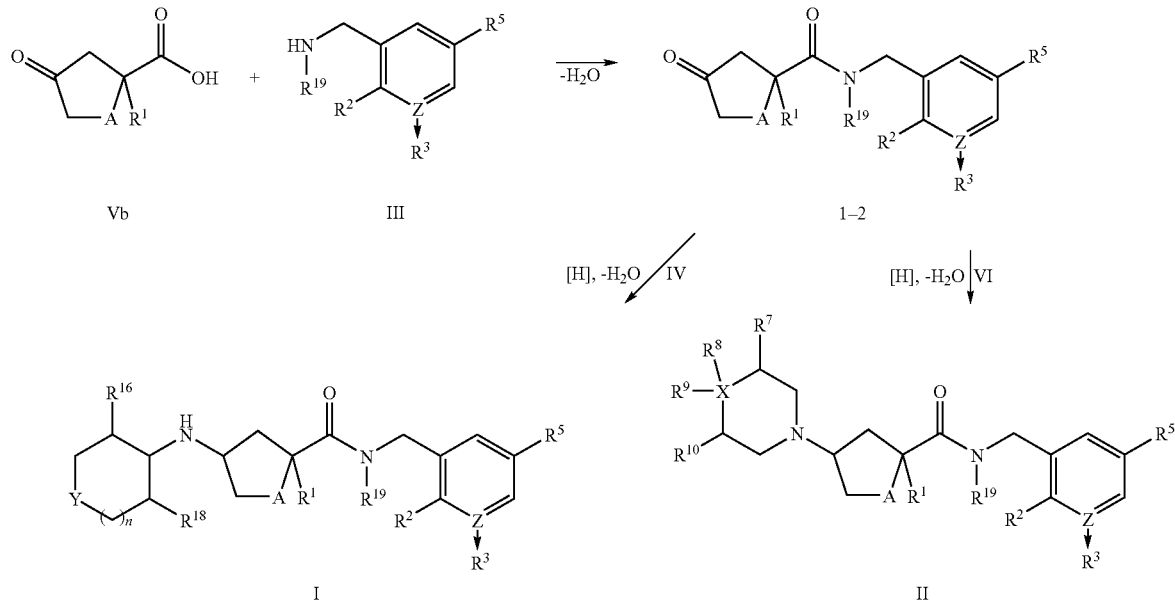

Intermediates of the formula V and their acid derivatives (Va and Vb) can be synthesized as shown in Scheme 3. α-Hetero under acidic conditions. If $P^1$ is benzyl, deprotection can be achieved by hydrogenolysis.

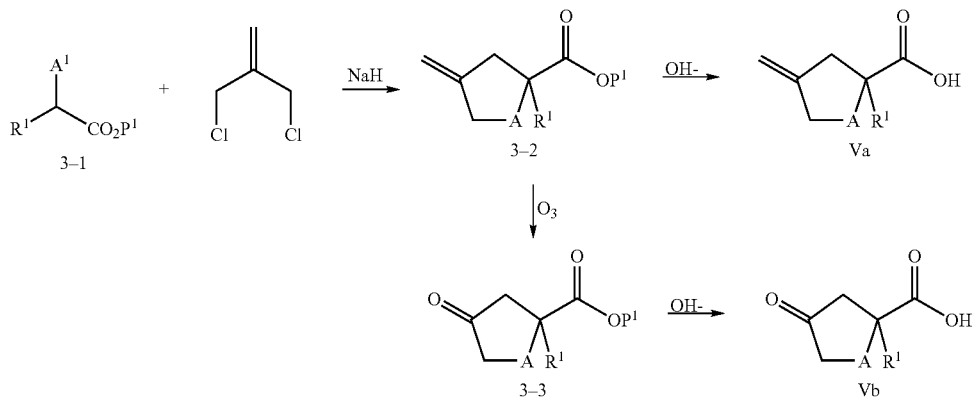

In some cases the order of carrying out the foregoing reaction schemes may be varied to facilitate the reaction or to avoid unwanted reaction products.

The following are representative procedures for the preparation of the compounds used in the following Examples or which can be substituted for the compounds used in the following Examples which may not be commercially available.

INTERMEDIATE 1

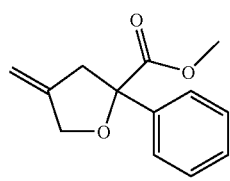

To a solution of methyl mandelate (10.0 mmol, 1.66 g), 3-chloro-2-chloromethyl-1-propene (10.0 mmol, 1.25 g) in DMF (30 mL), at 0° C., was added sodium hydride (60% in oil, 600 mg). The reaction was allowed to warm to room temperature, where a slight exotherm, warming the solution to ~40° C. was observed. The reaction mixture was allowed to stir at room temperature for 1 h. The reaction mixture was poured into dilute aqueous HCl and extracted with ethyl acetate. The organic layer was washed with water, aqueous saturated sodium bicarbonate, and then brine. The solution was dried, evaporated, and then purified by MPLC (20% Ethyl acetate/hexanes) to give 820 mg (38%) of the desired product.

H-NMR (300 MHz, CDCl$_3$) δ 7.54-7.30 (m, 5H); 5.06-5.02 (m, 1H); 4.95-4.93 (m, 1H); 4.57-4.54 (m, 2H); 3.71 (s, 3H); 3.49 (d, J=16 Hz, 1H); 2.93 (d, J=16 Hz, 1H).

INTERMEDIATE 2

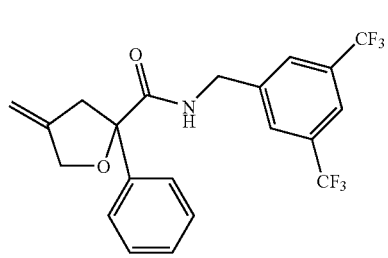

Intermediate 2 was synthesized according to the procedure described in Example 1, Step E, except that the product from Example 1, Step F was replaced with Intermediate 1.

INTERMEDIATE 3

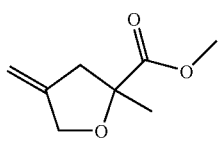

Intermediate 3 was synthesized according to the procedure described for the synthesis of Intermediate 1, except that methyl (R)-lactate was used in place of methyl mandelate.
H-NMR (300 MHz, CDCl$_3$) δ 5.00-4.97 (m, 1H); 4.93-4.90 (m, 1H); 4.47-4.45 (m, 2H); 3.74 (s, 3H); 2.98 (d, J=16 Hz, 1H); 2.52 (d, J=16 Hz, 1H); 1.51 (s, 3H).

INTERMEDIATE 4

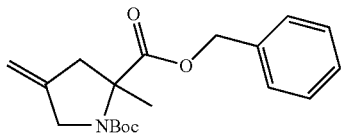

Intermediate 4 was synthesized according to the procedure described for the synthesis of Intermediate 1, except that N-Boc-Ala-OBn was used in place of methyl mandelate.

INTERMEDIATE 5

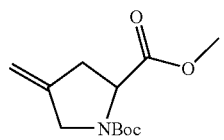

Intermediate 5 was synthesized according to the procedure described for the synthesis of Intermediate 1, except that N-Boc-Gly-OBn was used in place of methyl mandelate.

INTERMEDIATE 6

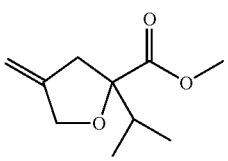

Step A

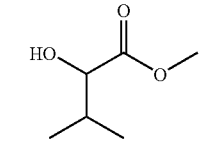

Thionyl chloride (15.5 mL) was added dropwise to methanol (30 mL) at −60° C. The resulting solution was added to a solution of 2-hydroxy-3-methylbutyric acid (42 mmol, 5.0 g) in methanol (100 mL). The resulting reaction mixture was allowed to stir overnight at room temperature before being concentrated under reduced pressure to give 4.5 g of the desired product. The product was used directly in the next step without further purification.

Step B

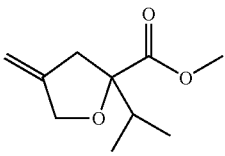

Intermediate 6 was synthesized according to the procedure described in Intermediate 1, except that the product form Step A was used in place of methyl mandelate.

INTERMEDIATE 7

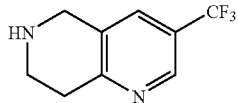

Step A

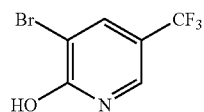

To a solution of 5-trifluoromethyl-2-pyridinal (51 g, 310 mmol) and sodium acetate (26.2 g, 319 mmol) in glacial acetic acid (200 mL) was added bromine (16.7 mL, 325 mmol) and the resulting mixture was heated at 80° C. for 2.5 h. The reaction was allow to cool to room temperature and then was evaporated under reduced pressure. The residue was neutralized with saturated NaHCO$_3$ solution and extracted with ethyl acetate (3×200 mL). The organics were combined, dried over MgSO$_4$, filtered, and evaporated in vacuo to yield 74.45 g (98%) of the crude product. $^1$H NMR (400 MHz, CDCl$_3$) δ 8.04 (d, J=2.6 Hz, 1H), 7.89 (m, 1H).

Step B

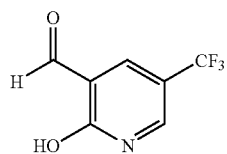

Under nitrogen, the substituted pyridine described in Step A, Intermediate 8 (48.8 g, 202 mmol) was added in small portions to a suspension of NaH (8.9 g, 220 mmol) in anhydrous tetrahydrofuran (500 mL). After complete addition of the intermediate, the reaction mixture was cooled to −78° C. and treated with tert-butyllithium (260 mL, 444 mmol) added dropwise via syringe. After stirring for 5 min, N,N-dimethylformamide (50 mL, 707 mmol) was added slowly to maintain the temperature below −50° C. The resulting mixture was then stirred for 10 h allowing it to warm to room temperature. The mixture was quenched with 2 N HCl and then diluted with ethyl acetate (1000 mL). The organic layer was separated, washed with brine, dried over MgSO4, and evaporated in vacuo. The desired product was precipitated out of ethyl acetate and hexanes and filtered to yield a light brown solid (28.55 g, 74%). $^1$H NMR (500 MHz, CD$_3$OD) δ 10.13 (s, 1H), 8.21 (s, 2H).

Step C

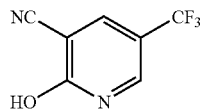

A mixture of the intermediate from Step B, Intermediate 8 (18 g, 95 mmol), sodium formate (7.1 g, 110 mmol), hydroxylamine hydrochloride (7.3 g, 110 mmol), and formic acid (150 mL) was stirred at room temperature for 2 h and then heated to reflux overnight. The reaction mixture was cooled and allowed to stand at room temperature for 7 days. The reaction was poured into water and extracted with ethyl acetate (3×). The combined organic layers were washed with water (2×), saturated NaHCO$_3$ and brine, dried over Na$_2$SO$_4$, filtered, and concentrated in vacuo to yield the desired product as a brown powder (17.84 g, 90%). $^1$H NMR (400 MHz, CD$_3$OD) δ 8.37 (d, J=2.7 Hz, 1H), 8.19 (q, J=0.7 Hz, 0.3 Hz, 1H).

Step D

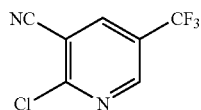

To a mixture of phosphorous oxychloride (13.4 mL, 144 mmol) and quinoline (8.7 mL, 73 mmol) was added the product from Step C, Intermediate 8, (24.6 g, 131 mmol) and the resulting mixture was heated to reflux for 3 h. The reaction was cooled to 100° C. before water (70 mL) was slowly added. The mixture was further cooled to room temperature and neutralized carefully with saturated NaHCO$_3$ solution. The aqueous layer was extracted with ethyl acetate (3×) and the organic layers were combined, dried over MgSO$_4$, filtered, and evaporated in vacuo. The crude product was purified by flash chromatography to afford (23.5 g, 87%) of the desired compound. $^1$H NMR (500 MHz, CDCl$_3$) δ 8.88 (d, J=2.0 Hz, 1H), 8.26 (d, J=2.5 Hz, 1H).

Step E

To a suspension of NaH (7.8 g, 200 mmol) in tetrahydrofuran (100 mL) under nitrogen was added dropwise a solution of tert-butyl methyl malonate (20 mL, 120 mmol) in anhydrous tetrahydrofuran (100 mL) via syringe. The reaction mixture was stirred for 0.5 h before a solution of the intermediate prepared in Step D, Intermediate 8 (20.1 g, 97.6 mmol) in tetrahydrofuran (200 mL) was added slowly via syringe. The reaction was stirred at room temperature overnight, then quenched with a saturated solution of $NH_4Cl$. The organic layer was separated and the aqueous layer was extracted with ethyl acetate (3×). The combined organic layers were washed with water (3×), dried over $Na_2SO_4$, filtered, and evaporated in vacuo. Flash chromatography afforded 31.76 g (95%) of the pure desired product. $^1$H NMR (500 MHz, $CDCl_3$) δ 9.03 (d, J=1.5 Hz, 1H), 8.25 (d, J=2.0 Hz, 1H), 5.25 (s, 1H), 3.86 (s, 3H), 1.52 (s, 9H).

Step F

A suspension of Raney Ni (1 g) and the product from Step E, Intermediate 8 (18.2 g, 52.9 mmol) in ethanol (130 mL) was placed on a Parr apparatus and hydrogenated at 40 psi $H_2$ overnight. The suspension was filtered through celite and the filtrate was evaporated in vacuo to afford 16.35 g (98%) of the crude product. $^1$H NMR (500 MHz, $CDCl_3$) δ 8.83 (s, 1H), 7.89 (s, 1H), 7.82 (s, 1H), 4.83 (d, J=16 Hz, 1H), 4.72 (s, 1H), 4.49 (d, J=16 Hz, 1H), 1.45 (s, 9H).

Step G

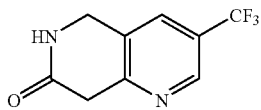

To the mixture of the product from Step F, Intermediate 8 (16 g, 51 mmol) in dichloromethane (60 mL) was added TFA (30 mL) and the resulting mixture was stirred at room temperature for 0.5 h. The solution was evaporated under reduced pressure and the residue was dissolved in dichloromethane. The mixture was neutralized by the slow addition of a solution of saturated sodium bicarbonate and the organic layer was removed. The aqueous layer was extracted with dichloromethane (4×) and the combined organic layers were dried over $Na_2SO_4$, filtered, and evaporated in vacuo to afford 10.42 g (95%) of the desired product. $^1$H NMR (400 MHz, $CDCl_3$) δ 8.81 (s, 1H), 7.78 (s, 1H), 7.30 (s, 1H), 4.63 (s, 2H), 3.90 (s, 2H).

Step H

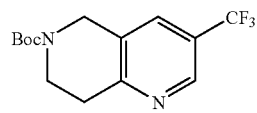

To a solution of the product from Step G, Intermediate 8 (18.0 g, 83.3 mmol) in tetrahydrofuran (50 mL) was added 1.0 M borane in tetrahydrofuran (417 mL, 420 mmol) and the resulting solution was stirred at room temperature overnight. The solution was evaporated under reduced pressure and the residue was treated with 1% HCl/methanol solution. The resulting mixture was heated at 50° C. overnight to breakdown the borane complex. Treatment with acidic methanol was repeated twice to insure that the borane complex was removed. A solution of this crude product (83.3 mmol, assuming 100% conversion) and diisopropylethylamine (43 mL, 250 mmol) in dichloromethane was treated with di-tert-butyl dicarbonate (36.4 g, 167 mmol) and the resulting mixture was stirred at room temperature overnight. The solution was washed with saturated sodium bicarbonate solution, water, and brine. The aqueous layers were combined and back-washed with dichloromethane (2×). The combined organic layers were then dried over $Na_2SO_4$, filtered, and evaporated to dryness. The crude product was purified by flash chromatography and MPLC to afford (11.89 g, 47%) as a yellow solid. $^1$H NMR (500 MHz, $CDCl_3$) δ 8.69 (s, 1H), 7.66 (s, 1H), 4.67 (s, 2H), 3.79 (t, J=6.0 Hz, 2H), 3.08 (t, J=5.5 Hz, 2H), 1.51 (s, 9H).

Step I

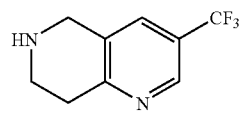

The product described in Step H, Intermediate 8 (11.89 g) was treated with a solution of 4 N HCl in dioxane. The solution was stirred at room temperature for 2 h and then evaporated in vacuo to afford Intermediate 8 (10.85 g, 99%) as a yellow powder. LC-MS for $C_9H_{10}F_3N_2$ calculated 202.07, found $[M+H]^+$ 203.0.

INTERMEDIATE 8

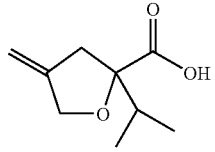

Intermediate 6 (700 mg, 3.8 mmol) was combined with lithium hydroxide (monohydrate, 240 mg, 5.8 mmol) in THF (8 mL) and methanol (6 mL). The reaction mixture was heated to 85° C. overnight before being cooled and concentrated to a small volume. Ethyl ether and water were added and the aqueous layer was acidified with 2 N HCl. The product was then extracted with ethyl acetate (3×). The combined organic extracts were washed with brine, dried, and evaporated to dryness to give 530 mg of the desired product (82%).

INTERMEDIATE 9

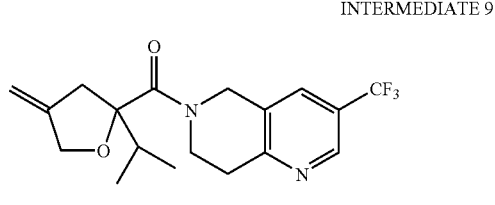

Intermediate 8 (530 mg, 3.11 mmol) was combined with Intermediate 7 (855 mg, 3.11 mmol), PyBrop (1.52 g, 3.26 mmol), and triethylamine (2.61 mL, 18.7 mmol) in DCM (20 mL). The resulting reaction mixture was stirred at room temperature overnight before being filtered. The filtrate was evaporated and the product was purified by MPLC (15% EA/hexanes) to give 719 mg of the desired product (65%). LC-MS C18H21F3N2O2: 354.37; Found 355.

INTERMEDIATE 10

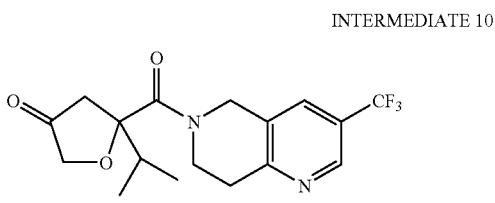

Intermediate 6 (719 mg, 2.03 mmol) was dissolved in pyridine (573 μL) and DCM (12 mL). The resulting solution was cooled to −78° C. and ozone was bubbled through the solution for 15 min before the ozonide was quenched with methyl sulfide (3 mL). The resulting mixture was allowed to stand at room temperature overnight before being evaporated to dryness. The crude material was purified by MPLC (25% EA/hexanes) to give 445 mg of the desired product.

INTERMEDIATE 11

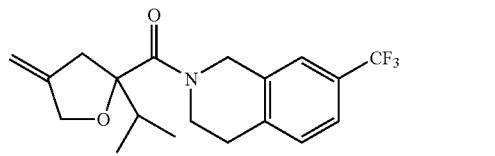

Intermediate 11 was synthesized according to the procedure described for the synthesis of Intermediate 9 except that Intermediate 13 was used in place of Intermediate 7.

INTERMEDIATE 12

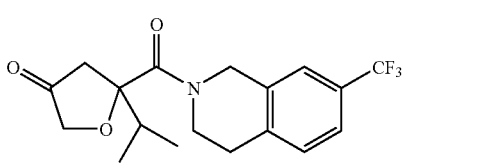

Intermediate 12 was synthesized according to the procedure described in Intermediate 10 except that Intermediate 11 was used in place of Intermediate 9.

Step A

INTERMEDIATE 13

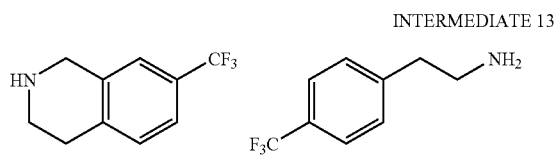

To a solution of 4-trifluoromethyl phenylacetonitrile (40 g, 215 mmol) in 2N NH3/MeOH (400 mL) was added Raney Ni (~4.0 g). The reaction mixture was placed in a par-shaker and shook under 50 Lb pressure overnight. The solution was filtered through celite and concentrated in vacuo to yield the desired amine (38 g, 95%). ESI-MS calc. For C9H10F3N: 189; Found: 190 (M+H).

Step B

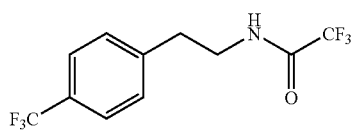

The above amine (Step A, Intermediate 13) (38 g, 200 mmol) and DIEA (52 mL, 300 mmol) were dissolved in DCM (300 mL). The solution was cooled to 0° C. before TFAA (36 mL, 250 mmol) was added slowly. The reaction mixture was stirred in the ice bath for another 10 minutes before warmed up to room temperature. The reaction was completed in 30 minutes and dumped in water and extracted with DCM (2×). The organic layer was washed with 1N HCl and saturated NaCl solution, dried over MgSO4, and concentrated in vacuo to yield the desired amide (56 g, 98%). ESI-MS calc. For C11H9F6NO: 285; Found: 286 (M+H).

Step C

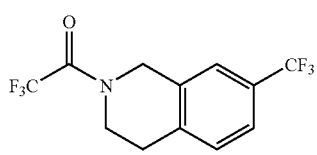

To a mixture of the amide (Step B, Intermediate 13) (73 g, 256 mmol) and paraformaldehyde (11.5 g, 385 mmol) was added 200 mL of acetic acid. The reaction mixture was stirred at room temperature for 5 min before concentrated sulfuric acid (200 mL). An exothermic reaction was observed. After 30 min, TLC showed a complete conversion. The mixture was cooled to RT before poured onto ice water (2000 mL) and extracted with EtOAc (3×500 mL). Combined organic layers were washed with water (2×), saturated NaHCO3, and brine, dried over MgSO4, filtered, evaporated and dried in vacuum. The desired amide (72.7 g, 96%) was obtained as a light-yellow solid. 1H NMR (400 MHz, CDCl3) δ 7.22 (q, J=11.67 Hz, 8.46 Hz, 1H), 7.11 (t, J=10.53 Hz, 1H), 7.03 (d, J=11.67 Hz, 1H), 4.79 (d, J=23.57 Hz, 2H), 3.91 (t, J=6.18 Hz, 1H), 3.87 (t, J=5.72 Hz, 1H), 2.97 (m, 2H). ESI-MS calc. For C12H9F6NO: 297; Found: 298 (M+H).

Step D

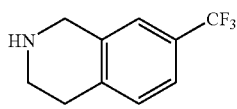

The amide (Step C, Intermediate 13) (50 g, 168 mmol) was dissolved in EtOH (200 mL) before solid K$_2$CO$_3$ (50 g, 360 mmol) and H$_2$O (50 mL) were added. The reaction mixture was refluxed for 15 hours before concentrated was vacuo. The concentrate was diluted with H$_2$O (100 mL) and extracted with DCM (5×). Combined organic layers were dried over MgSO$_4$, filtered, concentrated and purified on FC (10% [aq. NH4OH/MeOH 1/9]/DCM) to yield the amine (30 g, 89%). 1H NMR (400 MHz, CDCl3) δ 7.11 (d, J=8.4 Hz, 1H), 7.01 (bd, J=8.4 Hz, 1H), 6.89 (s, 1H), 4.03 (s, 2H), 3.15 (t, J=6.1 Hz, 2H), 2.80 (t, J=5.6 Hz, 2H), 1.80 (s, 1H). ESI-MS calc. For C10H10F3N: 201; Found: 202 (M+H).

INTERMEDIATE 14

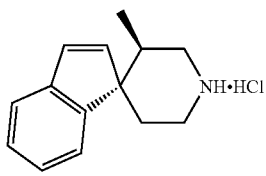

Step A

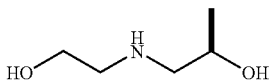

To a cooled (0° C.) solution of ethanolamine (41.8 g, 0.685 mol) in water (90 mL) was added neat (R)-propylene oxide (4.97 g, 85.6 mmol), dropwise. After 1 h at 0° C. the reaction was allowed to rise to rt and stirred overnight. The reaction mixture was concentrated at ~80° C. in vacuo to remove the water and most of the ethanolamine, to give 11.79 g of crude product, containing some residual ethanolamine. This material was used without further purification in Step B.

Step B

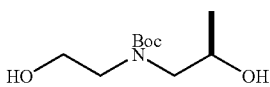

The diol prepared in Step A (11.8 g crude [~86% pure], ca. 83 mmol) was dissolved in DCM (150 mL) and treated with Boc$_2$O (23.4 g, 107 mmol) in DCM (75 mL) over 15 min. The reaction mixture was stirred over the weekend, concentrated, and purified by MPLC, eluting with 5% MeOH/EtOAc to provide 14.8 g (81%) of product.

Step C

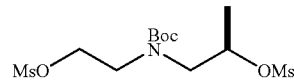

To a solution of the Boc-protected diol prepared in Step B (13.2 g, 60.3 mmol) and triethylamine (21.0 mL, 15.3 g, 151 mmol) in DCM (150 mL) at 0° C. was added dropwise methanesulfonyl chloride (9.56 mL, 14.1 g, 125 mmol). The reaction mixture was then stirred for 1.5 h, diluted with more DCM (100 mL) and washed with 3N HCl (250 mL). The aqueous layer was extracted again with DCM (200 mL), and the organic layers were combined and washed with 1N HCl (250 mL), saturated NaHCO$_3$ solution (250 mL), and brine (250 mL). The organic layer was dried over MgSO$_4$, filtered, and concentrated to give 22.8 g of crude bis-mesylate, which was used immediately. If not used immediately the bis-mesylate underwent decomposition.

Step D

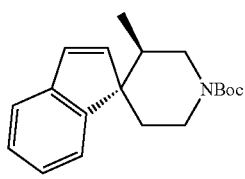

Indene (7.03 mL, 7.00 g, 60.3 mmol) was added dropwise over 4 min to a 1.0 M THF solution of LHMDS (127 mL, 127 mmol) at 0° C. After stirring for an additional 30 min., this solution was transferred via cannula to a solution of bis-mesylate (22.6 g, 60.3 mmol), prepared as described in Step C above, in THF (75 mL) at 0° C. The mixture was stirred for 2 h, warmed to rt and stirred overnight. The reaction mixture was partially concentrated and then partitioned between ethyl acetate and water. The organic layer was extracted again with ethyl acetate and the organic layers were combined. The organic phase was then washed with brine, dried over MgSO$_4$, filtered and concentrated to give 17.3 g of crude product. Purification by MPLC, eluting with 15% ethyl acetate/hexane, afforded 9.51 g (53%) of piperidine as a ~3:1 mixture of trans to cis (determined by H NMR). The mixture was crystallized from hot hexane to give 6 g (33%) of pure trans isomer (>20:1 by H NMR).

H NMR (CDCl$_3$, 400 MHz): 7.29 (dt, J=6.4, 1.6 Hz, 1H), 7.20 (m, 3H), 6.83 (d, J=6.0 Hz, 1H), 6.67 (d, J=5.6 Hz, 1H), 4.20 (br s, 2H), 2.97 (br t, J=3.2 Hz, 1H), 2.69 (br t, J=2.4 Hz, 1H), 2.16 (m, 1H), 2.07 (dt, J=4.4, 13.2 Hz, 1H), 1.49 (s, 9H), 1.25 (m, 1H), 0.31 (d, J=6.8 Hz, 3H).

Step E

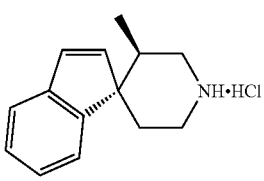

The Boc-piperidine prepared in Step D (4.35 g, 14.5 mmol) was dissolved in an anhydrous 4 N HCl solution in dioxane and stirred at rt for 1 h. The reaction mixture was then concentrated to afford 3.81 g of product. EI-MS calc. for C14H17N: 199; Found: 200 (M)+.

Example 1

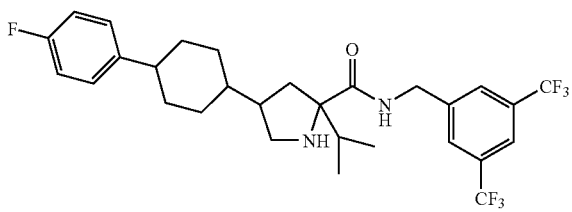

Step A

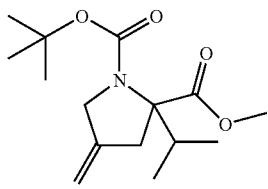

To a solution of N-(tert-butoxycarbonyl)-L-valine methyl ester (5 g, 22.7 mmol) and 3-chloro-2-chloromethyl-1-propene (2.63 mL, 22.7 mmol) in dry DMF (60 mL) cooled to 0° C. with ice/water bath under nitrogen atmosphere was added NaH (1.1 g, 22.7 mmol) and the resulting mixture stirred for 15 minutes. This was then followed by an addition of another 1.1 g of NaH for which the reaction was then stirred overnight, allowing to warm to room temperature. The reaction was quenched by pouring the contains into 1N HCl solution (100 mL). Extraction of the aqueous was done with ethyl acetate (250 mL), and the organics were then dried over sodium sulfate, filtered and concentrated in vacuo. Purification by flash column chromatography using a stepwise gradient eluant of 5% ethyl acetate/hexane to 20% ethyl acetate/hexane afforded the title compound as a clear oil. (Yield 5.25 g, 85%). $^1$H NMR (500 MHz, CDCl$_3$): 4.98-4.92 (m, 2H), 4.27 (d, J=14.8 Hz, 1H), 4.02 (br d, J=14.9 Hz, 1H), 3.68 (s, 3H), 2.82 (br d, J=16.3 Hz, 1H), 2.80-2.72 (m, 1H), 2.67 (dd, J=1.0, 16.3 Hz, 1H), 1.45 (s, 9H), 1.08 (d, J=6.6 Hz, 3H), 0.86 (d, J=6.8 Hz, 3H).

Step B

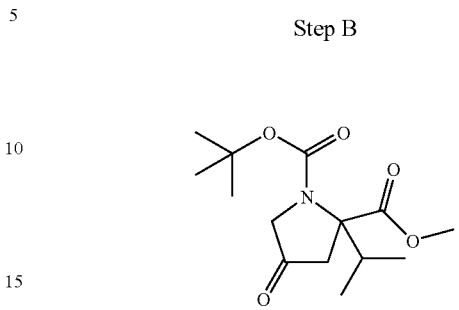

To a solution of the product from Step A, Example 1 (4.3 g, 15.18 mmol) in dry DCM (200 mL) cooled to −78° C. with dry ice/acetone bath was bubbled in ozone until the solution remained a slight blue color. Nitrogen gas was then bubbled in to displace the excess ozone which in turn cause the solution to loss its blue color and become clear. The dry ice/acetone bath was removed and methyl sulfide (16.8 mL, 227.73 mmol) was then added and the resulting solution was stirred until the reaction mixture warmed to room temperature. This was done to reduce the formed ozonide to the ketone. The mixture was concentrated in vacuo and then azeotroped with toluene until the odor of methyl sulfide was eliminated. No further purification was done and the material was used crude for the next reaction.

Step C

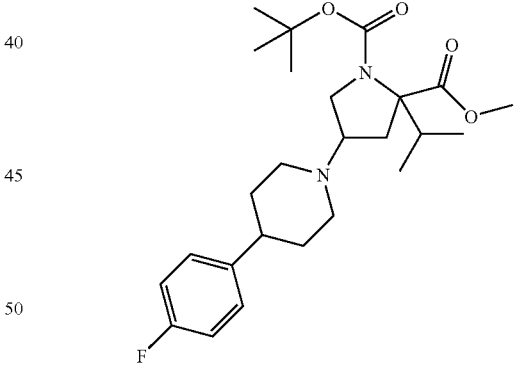

To a mixture of the compound described in Step B, Example 1 (1.10 g, 3.68 mmol), 4-fluorophenylpiperidine HCl salt (0.79 g, 3.68 mmol), molecular sieve (4 Å, 0.5 g), DIEA (642 μL, 3.68 mmol) in DCM (50 mL), was added sodium triacetoxyborohydride (3.90 g, 18.38 mmol) and the resulting mixture was stirred overnight at room temperature. The reaction was diluted with DCM, filtered through celite, and evaporated in vacuo. The residue was purified by preparative TLC (6×1000 micron, eluant: 0.5% aq. NH$_4$OH: 5% MeOH: 94.5% DCM) to yield the title compound as a yellow oil. (Yield 710 mg, 43%). LC-MS: calculated for C$_{25}$H$_{37}$FN$_2$O$_4$ is 448.27; found 471.1 (MNa)+ and 349 (MH-Boc)+.

Step D

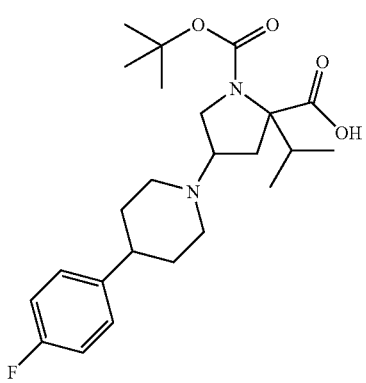

To a solution of the product from Step C, Example 1 (270 mg, 0.60 mmol) in THF:methanol:water (1:1:1 solution, 10 mL) was added solid LiOH (73 mg, 3.00 mmol) and the resulting mixture heated to 60° C. by oil bath and stirred overnight. The heating was turned off and the reaction mixture was allowed to cool to room temperature. Slow addition of 2N HCl solution was done until the pH of the mixture became neutral (pH~7). The mixture was concentrated in vacuo and then the residue was taken up in 97% DCM: 3% isopropanol. The solution was then dried over sodium sulfate, filtered and concentrated in vacuo to yield the title compound as an off-white foam. (Yield: 224 mg, 86%). LC-MS: calculated for $C_{24}H_{35}FN_2O_4$ is 434.27; found 457.2 $(MNa)^+$ and 335.2 $(MH-Boc)^+$.

Step E

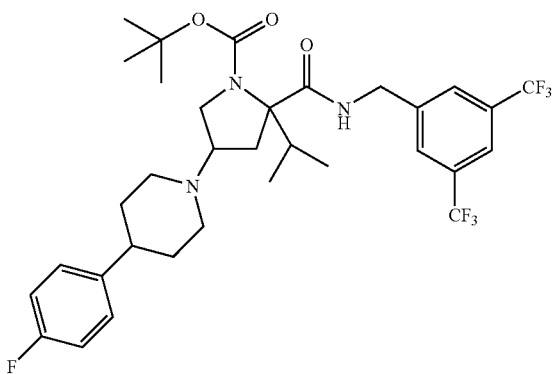

A mixture of the acid (described in Step D, Example 1, 100 mg, 0.23 mmol), 3,5-bis(trifluoromethyl)benzylamine hydrochloride (64 mg, 0.23 mmol), DMAP (2 mg, 0.015 mmol), N,N-diisopropyl ethylamine (40 μL, 0.23 mmol) in dichloromethane (10 mL) was treated with 1-[3-(dimethylamino)propyl]-3-ethylcarbodiimide hydrochloride (EDC, 88 mg, 0.46 mmol) and stirred at room temperature overnight. The reaction mixture was diluted with dichloromethane (10 mL), washed with water (2×10 mL), brine (1×15 mL), dried over anhydrous sodium sulfate and the solvent was evaporated. Purification by preparative TLC, eluant: 40% ethyl acetate/60% hexane, afforded two separate single isomers (isomer 1, less polar, 25 mg, 18%; isomer 2, more polar, 53 mg, 37%). LC-MS calculated for $C_{33}H_{40}F_7N_3O_3$ is 659.3, found 660.2 $(MH)^+$ and 560.2 $(MH-Boc)^+$ for both isomer 1 and isomer 2. $^1H$ NMR ($CDCl_3$, 500 MHz) (for Isomer 1) δ 9.22 (t, J=5.5 Hz, 1H), 7.78 (s, 1H), 7.69 (s, 2H), 7.19 (dd, J=5.5, 8.5 Hz, 2H), 6.99 (app t, J=8.5 Hz, 2H), 4.61 (dd, J=6.4, 15.8 Hz, 1H), 4.51 (dd, J=6.4, 15.8 Hz, 1H), 3.73 (dd, J=7.3, 9.4 Hz, 1H), 3.22 (br d, 11 Hz, 1H), 3.15 (t, J=10.2 Hz, 1H), 3.06 (p, 7.1 Hz, 1H), 2.96-2.86 (m, 2H), 2.70-2.60 (m, 4H), 1.66-1.56 (m, 1H), 1.45 (s, 9H), 0.90 (d, J=6.6 Hz, 3H), 0.84 (d, J=6.8 Hz, 3H).

NMR ($CDCl_3$, 500 MHz) (for Isomer 2) δ 9.23 (br s, 1H), 7.76 (s, 1H), 7.72 (s, 2H), 7.13-7.06 (m, 2H), 6.98 (app t, J=8.3 Hz, 2H), 4.65 (ddd, J=5.6, 15.6, 23 Hz, 1H), 4.50 (ddd, J=5.6, 15.5, 22.9 Hz, 1H), 4.30 (d, J=12.3 Hz, 1H), 3.78-3.70 (m, 1H), 3.44-3.35 (m, 1H), 3.23 (br d, 10.5 Hz, 1H), 3.20-3.00 (m, 2H), 2.85 (dd, J=6.7, 13.5 Hz, 1H), 2.74-2.68 (m, 1H), 2.51-2.42 (m, 1H), 2.12-1.96 (m, 2H), 1.88-1.72 (m, 1H), 1.45 (s, 9H), 0.88 (d, J=8.0 Hz, 3H), 0.86 (d, J=8.0 Hz, 3H).

Step F

Example 1-A

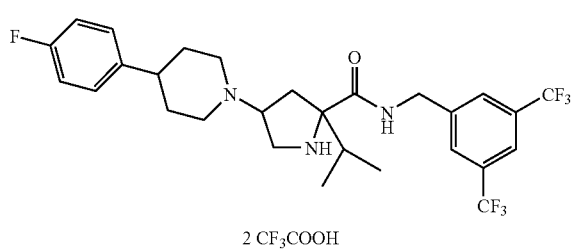

2 CF$_3$COOH

To a solution of the product (Isomer 1) from Step E, Example 1 (25 mg, 0.038 mmol) in DCM (1 mL) was added TFA (1 mL) and the resulting solution stirred for two hours. TLC showed no starting material left, and therefore, the mixture was concentrated in vacuo. The residue was taken up in DCM containing 5% hexane and concentrated again to dryness to give the titled compound as a white solid. (Yield 17 mg, 58%). LC-MS: calculated for $C_{28}H_{32}F_7N_3O_1$ is 559.27; found 560.2 $(MH)^+$.

Example 1-B

Step G

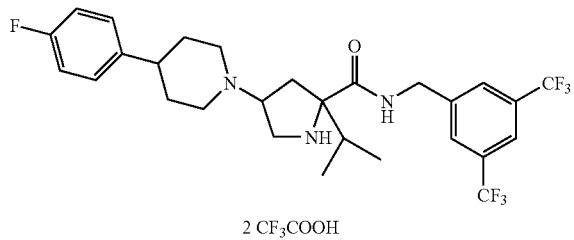

2 CF$_3$COOH

To a solution of the product (Isomer 2) from Step E, Example GJM-1 (60 mg, 0.091 mmol) in DCM (1 mL) was added TFA (1 mL) and the resulting solution stirred for two hours. TLC showed no starting material left, and therefore, the mixture was concentrated in vacuo. The residue was taken up in DCM containing 5% hexane and concentrated again to dryness to give the titled compound as a white solid. (Yield 42 mg, 70%). LC-MS: calculated for $C_{28}H_{32}F_7N_3O_1$ is 559.27; found 560.2 (MH)+.

Example 2

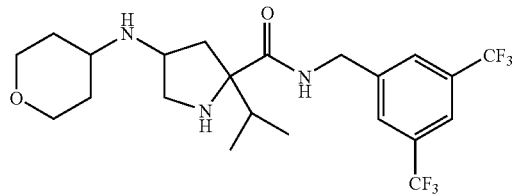

Step A

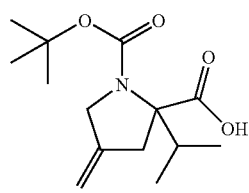

To a solution of the product from Step A, Example 1 (1.0 g, 3.53 mmol) in THF:methanol:water (1:1:1 solution, 40 mL) was added solid LiOH (424 mg, 17.65 mmol) and the resulting mixture heated to 60° C. by oil bath and stirred overnight. The heating was turned off and the reaction mixture was allowed to cool to room temperature. Slow addition of 2N HCl solution was done until the pH of the mixture became neutral (pH~7). The mixture was concentrated in vacuo and then the residue was taken up in 97% DCM: 3% isopropanol. The solution was then dried over sodium sulfate, filtered and concentrated in vacuo to yield the title compound as an oil. (Yield: 826 mg, 87%). $^1$H NMR (500 MHz, CDCl$_3$): 4.98-4.92 (m, 2H), 4.27 (d, J=14.6 Hz, 1H), 4.04 (br d, J=14.6 Hz, 1H), 2.82 (br d, J=15.8 Hz, 1H), 2.80-2.72 (m, 1H), 2.67 (br d, J=16 Hz, 1H), 1.45 (s, 9H), 1.08 (d, J=6.8 Hz, 3H), 0.88 (d, J=6.8 Hz, 3H).

Step B

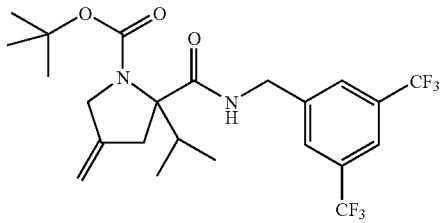

A mixture of the acid (described in step A, Example 2, 270 mg, 1.00 mmol), 3,5-bis(trifluoromethyl)benzylamine hydrochloride (280 mg, 1.00 mmol), DMAP (12 mg, 0.10 mmol), N,N-diisopropyl ethylamine (175□, 1.00 mmol) in dichloromethane (10 mL) was treated with 1-[3-(dimethylamino)propyl]-3-ethylcarbodiimide hydrochloride (EDC, 383 mg, 2.00 mmol) and stirred at room temperature overnight The reaction mixture was diluted with dichloromethane (10 mL), washed with water (2×10 mL), brine (1×15 mL), dried over anhydrous sodium sulfate and the solvent was evaporated. Purification by preparative TLC, eluant: 20% ethyl acetate/80% hexane, afforded the title compound as a white foam. (Yield 360 mg, 68%). LC-MS calculated for $C_{23}H_{28}F_6N_2O_3$ is 494.2, found 517.2 (MNa)+. $^1$H NMR (CDCl$_3$, 500 MHz) δ 9.04 (br s, 1H), 7.76 (s, 1H), 7.67 (s, 2H), 5.05 (s, 1H), 4.96 (s, 1H), 4.58 (dd, J=6.7, 15.6 Hz, 1H), 4.51 (dd, J=6.6, 15.7 Hz, 1H), 4.08 (d, J=14.6 Hz, 1H), 3.94 (d, J=14.6 Hz, 1H), 3.34 (d, 15.2 Hz, 1H), 3.14 (p, 6.8 Hz, 1H), 2.48 (br d, J=15.0 Hz, 1H), 1.45 (s, 9H), 0.90 (d, J=6.7 Hz, 3H), 0.84 (d, J=6.8 Hz, 3H).

Step C

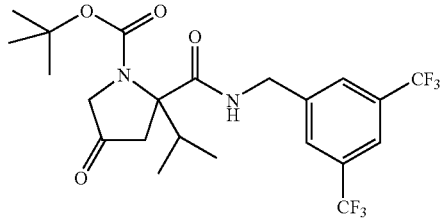

To a solution of the product from Step B, Example 2 (300 mg, 0.67 mmol) in dry DCM (5 mL) cooled to −78° C. with dry ice/acetone bath was bubbled in ozone until the solution remained a slight blue color. Nitrogen gas was then bubbled in to displace the excess ozone which in turn cause the solution to loss its blue color and become clear. The dry ice/acetone bath was removed and methyl sulfide (74 μL, 10.05 mmol) was then added and the resulting solution was stirred until the reaction mixture warmed to room temperature. This was done to reduce the formed ozonide to the ketone. The mixture was concentrated in vacuo and then azeotroped with toluene until the odor of methyl sulfide was eliminated. No further purification was done and the material was used crude for the next reaction.

Step D

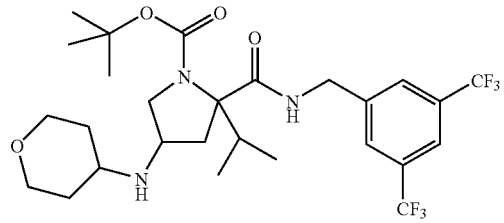

To a mixture of the compound described in Step C, Example 2 (240 mg, 0.455 mmol), 4-amino tetrahydrofuran HCl salt (63 mg, 0.455 mmol), molecular sieve (4 Å, 200 mg), DIEA (70 μL, 0.455 mmol) in DCM (15 mL), was added sodium triacetoxyborohydride (482 mg, 2.275 mmol) and the resulting mixture was stirred overnight at room temperature. The reaction was diluted with DCM, filtered through celite, and evaporated in vacuo. The residue was purified by preparative TLC (1000 micron, eluant: 6% MeOH: 94% DCM) to afford two separate single isomers (isomer 1, less polar, 75 mg, 28%; isomer 2, more polar, 58 mg, 22%). LC-MS calculated for $C_{27}H_{37}F_6N_3O_4$ is 581.27, found 582.3 (MH)⁺ and 482.2 (MH-Boc)⁺ for both isomer 1 and isomer 2.

Example 2-A

Step E

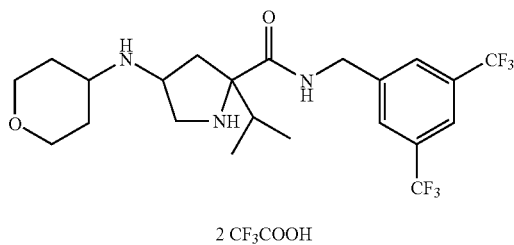

2 CF₃COOH

To a solution of the product (isomer 1) from Step D, Example 2 (70 mg, 0.120 mmol) in DCM (1.5 mL) was added TFA (1.5 mL) and the resulting solution stirred for two hours. TLC showed no starting material left, and therefore, the mixture was concentrated in vacuo. The residue was taken up in DCM containing 5% hexane and concentrated again to dryness to give the titled compound as a white solid. (Yield 79 mg, 93%). LC-MS: calculated for $C_{22}H_{29}F_6N_3O_2$ is 481.27; found 482.2 (MH)⁺.

Example 2-B

Step F

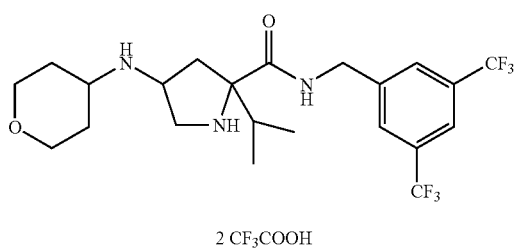

2 CF₃COOH

To a solution of the product (isomer 2) from Step D, Example 2 (53 mg, 0.90 mmol) in DCM (1.5 mL) was added TFA (1.5 mL) and the resulting solution stirred for two hours. TLC showed no starting material left, and therefore, the mixture was concentrated in vacuo. The residue was taken up in DCM containing 5% hexane and concentrated again to dryness to give the titled compound as a white solid. (Yield 60 mg, 94%). LC-MS: calculated for $C_{22}H_{29}F_6N_3O_2$ is 481.27; found 482.3 (MH)⁺.

Example 3

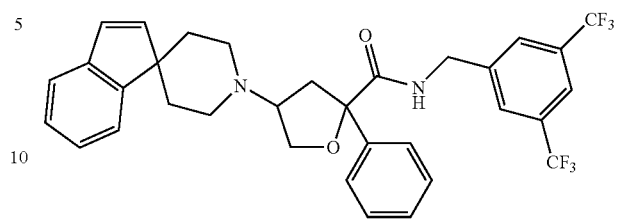

Intermediate 2 (410 mg, 0.68 mmol) was subject to standard ozonolysis conditions. The resulting ozonide was combined with 4-spiroindene-piperidine hydrochloride (150 mg, 0.68 mmol), diisopropylethylamine (237 μL, 1.36 mmol), sodium triacetoxyborohydride (721 mg, 3.40 mmol), and 4 Å molecular sieves, in DCM. The resulting reaction mixture was stirred for 4 days at room temperature before being filtered through celite and quenched with saturated aqueous sodium bicarbonate. The resulting mixture was washed with water (3×) and brine and dried over MgSO₄. The resulting material was purified by preparative TLC (60% ethyl acetate/hexanes) to give 11 mg of the desired product.

Example 4

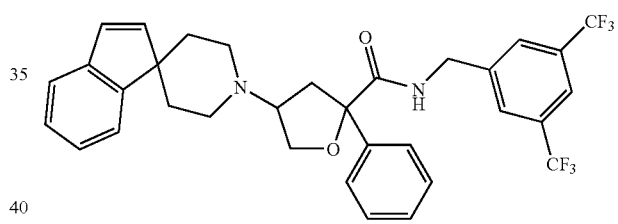

Example 2 was synthesized according to the procedure described in Example 1, except that 4-phenyl-piperidine hydrochloride was used in place of 4-spiroindene-piperidine hydrochloride.

Example 5

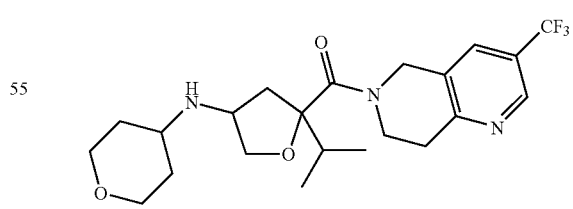

Intermediate 9 (192 mg, 0.538 mmol) was combined with 4-aminotetrahydropyran hydrochloride (81.4 mg, 0.592 mmol) and diisopropylethylamine (113 μL, 0.946 mmol) in Ti(OiPr)₄ (3.5 mL). The resulting solution was stirred overnight at room temperature. Sodium borohydride (41 mg, 1.1 mmol) and methanol (2 mL) were added and the mixture was stirred at room temperature for 30 min. Water was added and the solid was filtered off and washed with methanol. The combined filtrates were evaporated to dryness and the crude product was extracted with EA (×3) and purified by preparative TLC (10% MeOH/DCM) to give 12.5 mg of the title compound. LC-MS showed 441 (M+H). The 4 individual stereoisomers were isolated by HPLC on a ChiralPak AD column.

Example 6

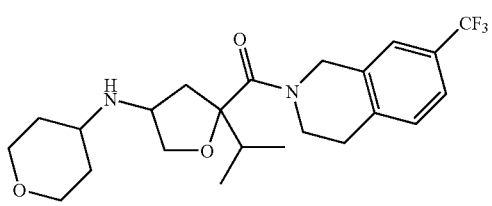

Example 4 was synthesized according to the procedure described in Example 3 except that Intermediate 11 was used in place of Intermediate 9. The cis and trans isomers were separated by Prep TLC (10% MeOH/DCM). LC-MS showed 440 (M+H).

Example 7

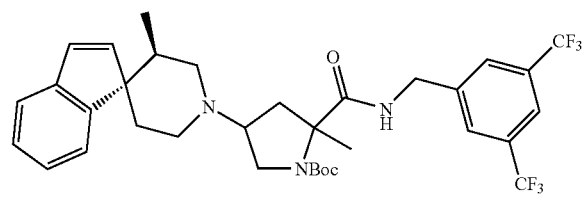

Step A

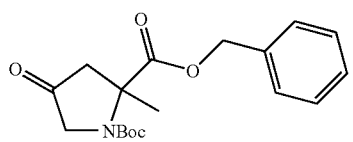

Intermediate 4 (502 mg, 1.52 mmol) was dissolved in DCM and cooled to −78° C. $O_3$ was bubbled through the solution until the clear/colorless solution turned bluish in color (~20 min). The solution was then purged with nitrogen and dimethylsulfide (1.11 mL, 15.2 mmol) was added and the mixture was allowed to warm to room temperature where it was stirred for 1 h before being concetrated to dryness. Recovered 485 mg.

Step B

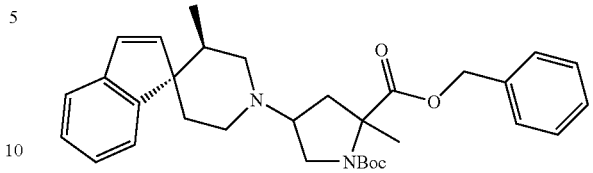

The product from Step A (485 mg, 1.52 mmol) was combined with Intermediate 14 (538 mg, 2.28 mmol), sodium triacetoxyborohydride (644 mg, 3.04 mmol), 4 Åmolecular sieves, and triethylamine (316 µL, 2.28 mmol) in DCM (20 mL). The resulting reaction mixture was stirred at room temperature for 3 days. The reaction mixture was filtered through celite, washed with saturated sodium bicarbonate and brine. The organic layer was dried over $MgSO_4$ and concentrated. The product was purified by prep TLC (0.2% $NH_4O$/1.8% MeOH/98% DCM) to give 367 mg of the desired product.
ESI-MS calc for C32H40N2O4=516; found 517.3.

Step C

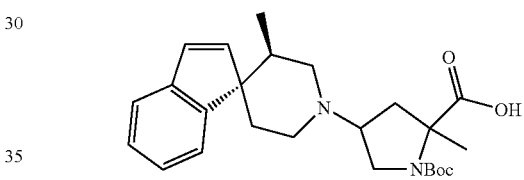

The product from Step B (359 mg, 0.696 mmol) was dissolved in MeOH (3 mL) and THF (3 mL). A solution of lithium hydroxide (monohydrate) (33 mg, 0.79 mmol) in water (3 mL) was added. The resulting reaction mixture was heated to 60° C. After 24 h an additional quantity of lithium hydroxide (17 mg, 0.41 mmol) was added. The resulting reaction mixture was stirred for an additional 24 h before being cooled to 0° C., where 1.0 M HCl in ether (1.2 mL) as added. The solution was concentrated to give 296 mg of the desired product.

Step D

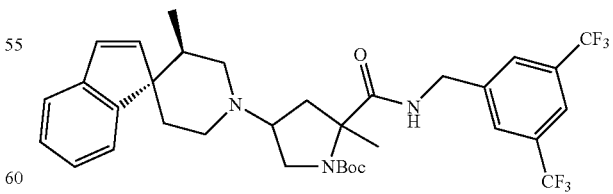

The product from Step C (148 mg, 0.347 mmol) was combined with 3,5-bis(trifluoromethyl)benzylamine hydrochloride (195 mg, 0.695 mmol), EDC (133 mg, 0.695 mmol), and triethylamine (96 µL, 0.70 mmol) in DCM (10 mL). The resulting solution was stirred overnight at room temperature. The reaction mixture was concentrated and the product was purified by prep TLC (0.5% NH$_4$OH/4.5% MeOH/95% DCM) to give 128 mg of the desired product. ESI-MS calculated for C34H39N3O3F6=651; found 652.3.

Example 8

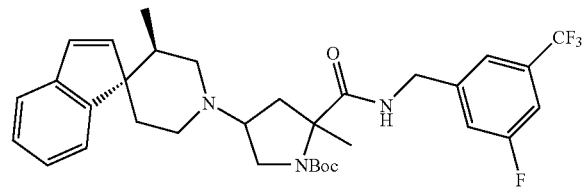

Example 8 was prepared according to the procedure described for Example 7 except that 3,5-bis(trifluoromethyl)benzylamine hydrochloride was replaced with 3-fluoro-5-trifluoromethylbenzylamine hydrochloride in Step D. Recovered 123 mg. ESI-MS calculated for C33H39N3O3F4=601; found 602.35.

Example 9

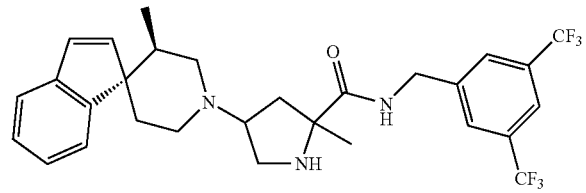

Example 7 (120 mg, 0.184 mmol) was dissolved in 4 M HCl in dioxane (1 mL) and was stirred at room temperature for several hours before being concentrated to dryness. Recovered 114 mg of the desired HCl salt. ESI-MS calculated for C29H31N3OF6=551; found 552.25.

Example 10

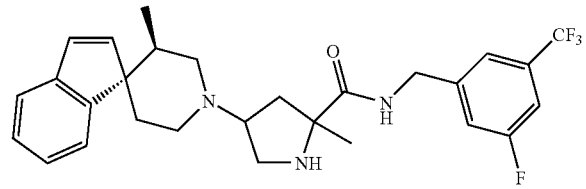

Example 8 (116 mg, 0.193 mmol) was dissolved in 4 M HCl in dioxane (1 mL) and was stirred at room temperature for several hours before being concetrated to dryness. Recovered 82 mg of the desired HCl salt. ESI-MS calculated for C29H31N3OF6=501; found 502.3.

Example 11

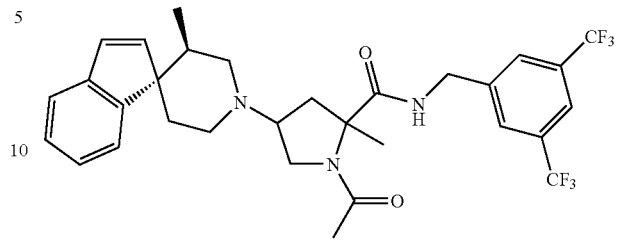

Example 9 (20 mg, 0.36) was dissovled in DCM (2 mL) and pyridine (51 µL, 0.73) was added followed by acetic anhydride (34 µL, 0.36 mmol). the reaction mixture was allowed to stir at room temperature. After ~18 h the mixture was concentrated and the product was purifed by prep TLC (02.% NH$_4$OH/1.8% MeOH/98% DCM) to give 17 mg of the desired product. ESI-MS calculated for C31H33N3O2F6=593; found 594.2.

Example 12

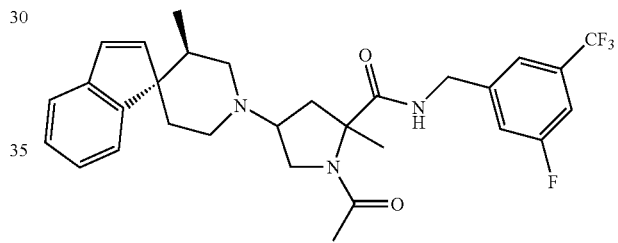

Example 12 was prepared according to the procedure described for Example 11, except that Example 9 was replaced with Example 10. Recovered 18 mg. ESI-MS calculated for C30H33N3O2F4=543; found 544.3.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound having the Formula IIa,

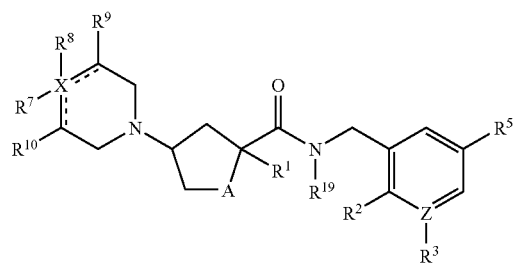

or a pharmaceutically acceptable salt thereof or an individual diastereomer thereof, wherein:

X and Z are C;

$R^1$ is selected from: —$C_{1-6}$alkyl unsubstituted or substituted with 1-6 substituents independently selected from halo, hydroxy, —O—$C_{1-3}$alkyl and trifluoromethyl; and phenyl unsubstituted or substituted with 1-3 substituents independently selected from halo, hydroxyl, $C_{1-3}$alkyl, $C_{1-3}$alkoxy and trifluoromethyl;

$R^2$ and $R^3$ are independently selected from: hydrogen, fluoro, chloro, and $C_{1-3}$alkyl unsubstituted or substituted with 1-3 fluoro;

$R^5$ is selected from fluoro, chloro, and —$C_{1-6}$alkyl unsubstituted or substituted with 1-6 substituents selected from fluoro;

$R^7$ is fluorophenyl;

$R^8$ is hydrogen;

or $R^7$ and $R^8$ join to form a 1H-indene ring, which is optionally substituted with 1-5 substituents independently selected from halo, trifluoromethyl, and $C_{1-3}$alkyl;

A is selected from —O— and —N($R^{20}$)—;

$R^9$ and $R^{10}$ are independently selected from: hydrogen and $C_{1-6}$alkyl;

$R^{19}$ is selected from: hydrogen and $C_{1-6}$ alkyl; and $R^{20}$ is selected from: hydrogen, $C_{1-6}$ alkyl, C(=O)CH$_3$, and BOC.

2. The compound of claim 1, wherein $R^1$ is selected from: —$C_{1-6}$alkkyl unsubstituted or substituted with 1-6 substituents independently selected from halo; and phenyl unsubstituted or substituted with 1-3 substituents independently selected from halo, $C_{1-3}$alkyl, and trifluoromethyl.

3. The compound of claim 1, wherein $R^2$ is H.

4. The compound of claim 1, wherein $R^3$ is selected from: trifluoromethyl, chloro, and fluoro.

5. The compound of claim 1, wherein $R^5$ is selected from hydrogen, trifluoromethyl, chloro and fluoro.

6. The compound of claim 1, where R7 and R8 join to form a 1H-indene ring, wherein said ring is unsubstituted.

7. The compound of claim 1, wherein $R^{19}$ and $R^2$ are H.

8. A compound selected from the group consisting of:

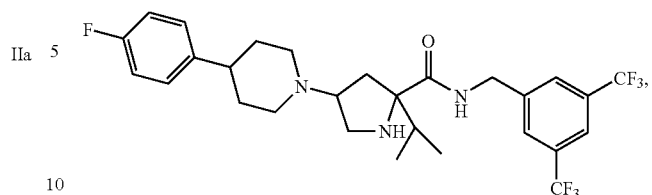

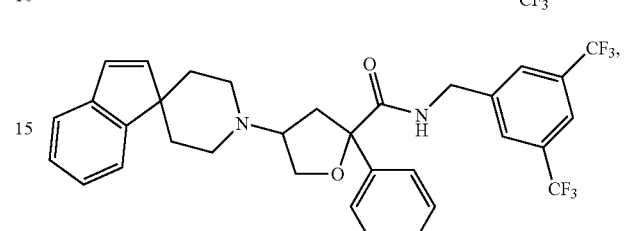

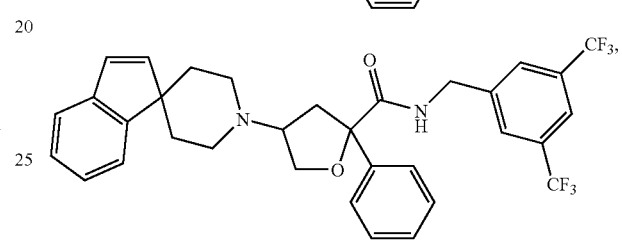

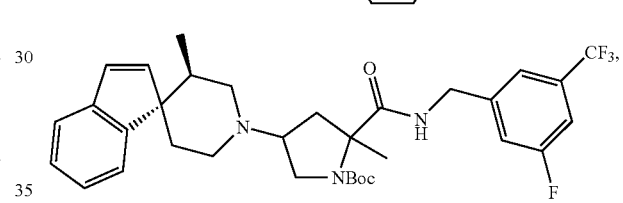

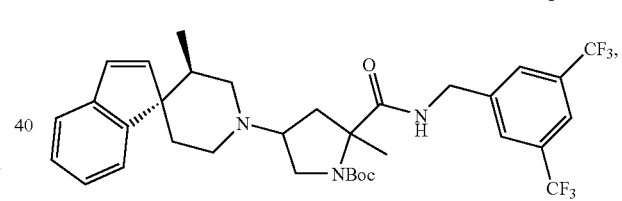

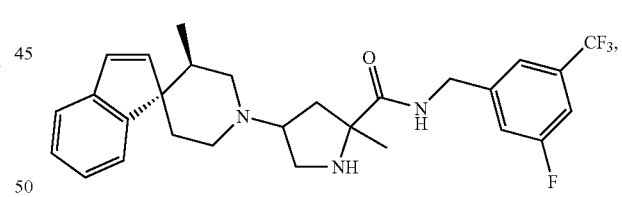

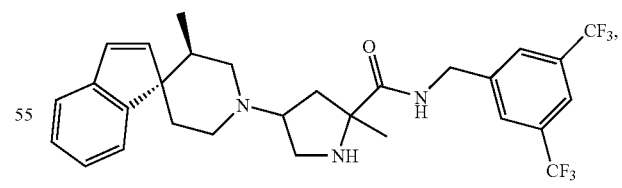

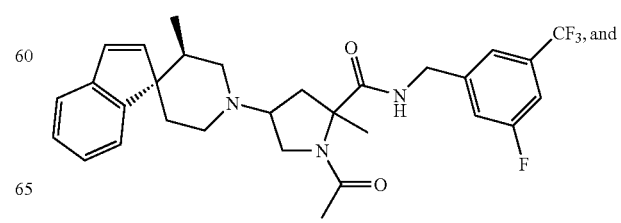

-continued
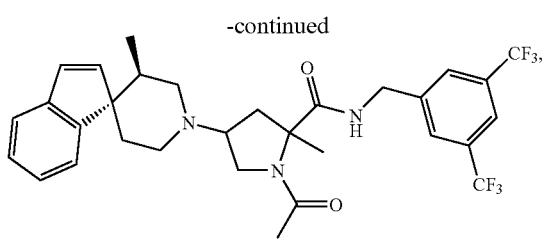
or a pharmaceutically acceptable salt thereof, or individual diastereomer thereof.
9. A pharmaceutical composition which comprises an inert carrier and the compound of claim 1.
10. A method for modulation of CCR-2 receptor activity in a mammal which comprises the administration of an effective amount of the compound of claim 1.
* * * * *